United States Patent
Dunman

(10) Patent No.: US 10,525,032 B2
(45) Date of Patent: Jan. 7, 2020

(54) ANTIMICROBIAL COMPOSITIONS COMPRISING MUPIROCIN AND NEOMYCIN

(71) Applicant: University of Rochester, Rochester, NY (US)

(72) Inventor: Paul M. Dunman, Pittsford, NY (US)

(73) Assignee: UNIVERSITY OF ROCHESTER, Rochester, NY (US)

(*) Notice: Subject to any disclaimer, the term of this patent is extended or adjusted under 35 U.S.C. 154(b) by 0 days.

(21) Appl. No.: 15/749,578

(22) PCT Filed: Aug. 3, 2016

(86) PCT No.: PCT/US2016/045258
§ 371 (c)(1),
(2) Date: Feb. 1, 2018

(87) PCT Pub. No.: WO2017/023977
PCT Pub. Date: Feb. 9, 2017

(65) Prior Publication Data
US 2018/0228760 A1    Aug. 16, 2018

Related U.S. Application Data

(60) Provisional application No. 62/201,380, filed on Aug. 5, 2015.

(51) Int. Cl.
| | | |
|---|---|---|
| *A61K 31/351* | (2006.01) | |
| *A61K 9/00* | (2006.01) | |
| *A61K 9/06* | (2006.01) | |
| *A61K 9/107* | (2006.01) | |
| *A61P 17/02* | (2006.01) | |
| *A61P 31/04* | (2006.01) | |
| *A61K 45/06* | (2006.01) | |
| *A61K 31/7036* | (2006.01) | |
| *A61K 47/10* | (2017.01) | |

(52) U.S. Cl.
CPC .......... *A61K 31/351* (2013.01); *A61K 9/0014* (2013.01); *A61K 9/06* (2013.01); *A61K 9/107* (2013.01); *A61K 31/7036* (2013.01); *A61K 45/06* (2013.01); *A61K 47/10* (2013.01); *A61P 17/02* (2018.01); *A61P 31/04* (2018.01); *A61K 2300/00* (2013.01); *Y02A 50/473* (2018.01)

(58) Field of Classification Search
CPC ...... A61K 31/351; A61K 9/0014; A61K 9/06; A61K 9/107; A61K 31/7036; A61K 2300/00; A61P 17/02; A61P 31/04
USPC ........................................................... 514/39
See application file for complete search history.

(56) References Cited

U.S. PATENT DOCUMENTS

2012/0108527 A1* 5/2012 Sawant ................ A61K 9/0014
514/24

FOREIGN PATENT DOCUMENTS

| WO | 2007014372 | 2/2007 |
|---|---|---|
| WO | 2012017215 | 2/2012 |

OTHER PUBLICATIONS

Boyce et al. Noncytotoxic Combinations of Topical Antimicrobial Agents for Use with Cultured Skin Substitutes. Antimicrobial Agents and Chemotherapy, Jun. 1995, vol. 39, No. 6, p. 1324-1328. (Year: 1995).*
Hughes J, Mellows G., "On the mode of action of pseudomonic acid: inhibition of protein synthesis in *Staphylococcus aureus*," The Journal of Antibiotics, 31:330-335 (1978).
Hughes J, Mellows G., "Inhibition of isoleucyl-transfer ribonucleic acid synthetase in *Escherichia coli* by pseudomonic acid," The Biochemical Journal 176:305-318 (1978).
Hughes J, Mellows G., "Interaction of pseudomonic acid A with *Escherichia coli* B isoleucyl-tRNA synthetase," The Biochemical Journal 191:209-219 (1980).
Sutherland R, Boon RJ, Griffin KE, Masters PJ, Slocombe B, White AR., "Antibacterial activity of mupirocin (pseudomonic acid), a new antibiotic for topical use," Antimicrob Agents Chemother 27:495-498 (1985).
Beale AS, Gisby J, Sutherland R., "Efficacy of mupirocin calcium ointment in the treatment of experimental wound infections caused by methicillin-resistant strains of *Staphylococcus aureus*," Journal of Chemotherapy. 1 (4 Suppl):397-398 (1989).
Moy JA, Caldwell-Brown D, Lin AN, Pappa KA, Carter DM., Mupirocin-resistant *Staphylococcus aureus* after long-term treatment of patients with epidermolysis bullosa, Journal of the American Academy of Dermatology 22:893-895 (1990).
Rode H, de Wet PM, Millar AJ, Cywes S., Bactericidal efficacy of mupirocin in multi-antibiotic resistant *Staphylococcus aureus* burn wound infection, The Journal of Antimicrobial Chemotherapy 21:589-595 (1988).
Rode H, Hanslo D, de Wet PM, Millar AJ, Cywes S., "Efficacy of mupirocin in methicillin-resistant *Staphylococcus aureus* burn wound infection," Antimicrob Agents Chemother 33:1358-1361(1989).
Coates T, Bax R, Coates A., "Nasal decolonization of *Staphylococcus aureus* with mupirocin: strengths, weaknesses and future prospects," The Journal of Antimicrobial Chemotherapy 64:9-15 (2009).
Mupirocin Study Group, "Nasal mupirocin prevents *Staphylococcus aureus* exit-site infection during peritoneal dialysis," Journal of the American Society of Nephrology : JASN 7:2403-2408 (1996).
Gaspar MC, Uribe P, Sanchez P, Coello R, Cruzet F., "Hospital personnel who are nasal carriers of methicillin-resistant *Staphylococcus aureus*, Usefulness of treatment with mupirocin," Enfermedades Infecciosasy Microbiologia Clinica 10:107-110 (1992); (English Abstract).
Gernaat-van der Sluis AJ, Hoogenboom-Verdegaal AM, Edixhoven PJ, Spies-van Rooijen NH., "Prophylactic mupirocin could reduce orthopedic wound infections. 1,044 patients treated with mupirocin compared with 1,260 historical controls," Acta Orthopaedica Scandinavica 69:412-414(1998).

(Continued)

*Primary Examiner* — Yih-Horng Shiao
(74) *Attorney, Agent, or Firm* — Riverside Law LLP

(57) ABSTRACT

The present invention features a composition comprising mupirocin and neomycin, a formulation thereof and a method of treating microbial infection using the composition.

27 Claims, 9 Drawing Sheets

(56) References Cited

OTHER PUBLICATIONS

Kluytmans JA, Mouton JW, VandenBergh MF, Manders MJ, Maat AP, Wagenvoort JH, Michel MF, Verbrugh HA., "Reduction of surgical-site infections in cardiothoracic surgery by elimination of nasal carriage of *Staphylococcus aureus*," Infection Control and Hospital Epidemiology : the official journal of the Society of Hospital Epidemiologists of America 17:780-785 (1996).

Mackie DP, van Hertum WA, Schumburg TH, Kuijper EC, Knape P, Massaro F., "Reduction in *Staphylococcus aureus* wound colonization using nasal mupirocin and selective decontamination of the digestive tract in extensive burns," Burns : Journal of the International Society for Burn Injuries 20 Suppl 1:S14-17; discussion S17-18 (1994).

Talon D, Rouget C, Cailleaux V, Bailly P, Thouverez M, Barale F, Michel-Briand Y., "Nasal carriage of *Staphylococcus aureus* and cross-contamination in a surgical intensive care unit: efficacy of mupirocin ointment," The Journal of Hospital Infection 30:39-49 (1995).

Wenisch C, Laferl H, Szell M, Smolle KH, Grisold A, Bertha G, Krause R., "A holistic approach to MRSA eradication in critically ill patients with MRSA pneumonia," Infection 34:148-154 (2006).

Lee AA, Gizard Y, Empel J, Bonetti EJ, Harbarth S, Francois P., "Mupirocin-induced mutations in ileS in various genetic backgrounds of methicillin-resistant *Staphylococcus aureus*," J Clin Microbiol 52:3749-3754 (2014).

Fierobe L, Decre D, Muller C, Lucet JC, Marmuse JP, Mantz J, Desmonts JM., "Methicillin-resistant *Staphylococcus aureus* as a causative agent of postoperative intra-abdominal infection: relation to nasal colonization," Clin Infect Dis 29:1231-1238 (1999).

Seah C, Alexander DC, Louie L, Simor A, Low DE, Longtin J, Melano RG., "MupB, a new high-level mupirocin resistance mechanism in *Staphylococcus aureus*," Antimicrob Agents Chemother 56:1916-1920 (2012).

Hetem DJ, Bonten MJ., "Clinical relevance of mupirocin resistance in *Staphylococcus aureus*," The Journal of Hospital Infection 85:249-256 (2013).

Mikkelsen NE, Brannvall M, Virtanen A, Kirsebom LA. 1999. Inhibition of RNase P RNA cleavage by aminoglycosides. Proc Natl Acad Sci U S A 96:6155-6160.

Mikkelsen NE, Johansson K, Virtanen A, Kirsebom LA. 2001. Aminoglycoside binding displaces a divalent metal ion in a tRNA-neomycin B complex. Nature structural biology 8:510-514.

Tok JB, Cho J, Rando RR. 1999. Aminoglycoside antibiotics are able to specifically bind the 5'-untranslated region of thymidylate synthase messenger RNA. Biochemistry 38:199-206.

von Ahsen U, Davies J, Schroeder R. 1992. Non-competitive inhibition of group I intron RNA self-splicing by aminoglycoside antibiotics. Journal of molecular biology 226:935-941.

Eubank TD, Biswas R, Jovanovic M, Litovchick A, Lapidot A, Gopalan V. 2002. Inhibition of bacterial RNase P by aminoglycoside-arginine conjugates. FEBS letters 511:107-112.

Liu X, Chen Y, Fierke CA. 2014. A real-time fluorescence polarization activity assay to screen for inhibitors of bacterial ribonuclease P. Nucleic acids research 42:e159.

Boyce et al., 1995, "Noncytotoxic Combinations of Topical Antimicrobial Agents for Use with Cultured Skin Substitutes." Antimicrobial Agents and Chemotherapy, American Society for Microbiology, US, 39(6): 1324-1328.

Boyce et al., 1995, "Effective management of microbial contamination in cultured skin substitutes after grafting to athymic mice." Wound Repair and Regeneration. 5(2): 191-197.

Blanchard et al., 2016, "Neomycin Sulfate Improves the Antimicrobial Activity of Mupirocin-Based Antibacterial Ointments." Antimicrobial Agents and Chemotherapy. 60(2): 862-872.

Hendley et al., 2003, "Eradication of Resident Bacteria of Normal Human Skin by Antimicrobial Ointment." Antimicrobial Agents and Chemotherapy. 47(6): 1988-1990.

\* cited by examiner

ANTIMICROBIAL COMPOSITIONS COMPRISING MUPIROCIN AND NEOMYCIN

FIELD

The present invention provides a composition comprising mupirocin and neomycin for the prevention and treatment of microbial infections.

CROSS-REFERENCES TO RELATED APPLICATIONS

This application is a U.S. national phase application filed under 35 U.S.C. § 371 claiming benefit to International Patent Application No. PCT/US16/45258, filed Aug. 3, 2016, which is entitled to priority under 35 U.S.C. § 119(e) to U.S. Provisional Patent Application No. 62/201,380, filed Aug. 5, 2015, each of which application is hereby incorporated herein by reference in its entirety.

BACKGROUND OF THE INVENTION

Mupirocin is an antimicrobial agent that inhibits bacterial isoleucyl-tRNA synthetase mediated Ile-tRNA aminoacylation and, consequently protein translation. See Hughes J, Mellows G., "On the mode of action of pseudomonic acid: inhibition of protein synthesis in *Staphylococcus aureus*," *The Journal of Antibiotics*, 31:330-335 (1978); Hughes J, Mellows G., "Inhibition of isoleucyl-transfer ribonucleic acid synthetase in *Escherichia coli* by pseudomonic acid," *The Biochemical Journal* 176:305-318 (1978); Hughes J, Mellows G., "Interaction of pseudomonic acid A with *Escherichia coli* B isoleucyl-tRNA synthetase," *The Biochemical Journal* 191:209-219 (1980). The agent displays excellent antibacterial activity toward most Gram-positive species, lacks cross resistance to current antibiotics and is well absorbed in humans but is also rapidly degraded in vivo, and consequently is not ideal for systemic use. See Sutherland R, Boon R J, Griffin K E, Masters P J, Slocombe B, White A R., "Antibacterial activity of mupirocin (pseudomonic acid), a new antibiotic for topical use," *Antimicrob Agents Chemother* 27:495-498 (1985). However, mupirocin based ointments have proven effective for the treatment of *S. aureus* skin and wound infections and have also recently emerged as the standard of care for pre-surgical nasal decolonization. See Beale A S, Gisby J, Sutherland R., "Efficacy of mupirocin calcium ointment in the treatment of experimental wound infections caused by methicillin-resistant strains of *Staphylococcus aureus*," *Journal of Chemotherapy* (Florence, Italy) 1:397-398 (1989); Moy J A, Caldwell-Brown D, Lin A N, Pappa K A, Carter D M., "Mupirocin-resistant *Staphylococcus aureus* after long-term treatment of patients with epidermolysis bullosa, *Journal of the American Academy of Dermatology* 22:893-895 (1990); Rode H, de Wet P M, Millar A J, Cywes S., "Bactericidal efficacy of mupirocin in multi-antibiotic resistant *Staphylococcus aureus* burn wound infection, *The Journal of Antimicrobial Chemotherapy* 21:589-595 (1988); Rode H, Hanslo D, de Wet P M, Millar A J, Cywes S., "Efficacy of mupirocin in methicillin-resistant *Staphylococcus aureus* burn wound infection," *Antimicrob Agents Chemother* 33:1358-1361(1989); Coates T, Bax R, Coates A., "Nasal decolonization of *Staphylococcus aureus* with mupirocin: strengths, weaknesses and future prospects," *The Journal of Antimicrobial Chemotherapy* 64:9-15 (2009). Indeed, mupirocin mediated nasal decolonization has been shown to be effective in reducing burn wound infections, pulmonary infections, infections in dialysis patients, surgical site infections, orthopedic infections, and *S. aureus* transmission among healthcare workers and intensive care unit patients. See Mupirocin Study Group, "Nasal mupirocin prevents *Staphylococcus aureus* exit-site infection during peritoneal dialysis," *Journal of the American Society of Nephrology: JASN* 7:2403-2408 (1996); Gaspar M C, Uribe P, Sanchez P, Coello R, Cruzet F., "Hospital personnel who are nasal carriers of methicillin-resistant *Staphylococcus aureus*, Usefulness of treatment with mupirocin," *Enfermedades Infecciosas y Microbiologia Clinica* 10:107-110 (1992); Gernaat-van der Sluis A J, Hoogenboom-Verdegaal A M, Edixhoven P J, Spies-van Rooijen N H., "Prophylactic mupirocin could reduce orthopedic wound infections. 1,044 patients treated with mupirocin compared with 1,260 historical controls," *Acta Orthopaedica Scandinavica* 69:412-414(1998); Kluytmans J A, Mouton J W, VandenBergh M F, Manders M J, Maat A P, Wagenvoort J H, Michel M F, Verbrugh H A., "Reduction of surgical-site infections in cardiothoracic surgery by elimination of nasal carriage of *Staphylococcus aureus*," *Infection Control and Hospital Epidemiology: the official journal of the Society of Hospital Epidemiologists of America* 17:780-785 (1996); Mackie D P, van Hertum W A, Schumburg T H, Kuijper E C, Knape P, Massaro F., "Reduction in *Staphylococcus aureus* wound colonization using nasal mupirocin and selective decontamination of the digestive tract in extensive burns," *Burns: Journal of the International Society for Burn Injuries* 20 Suppl 1:S14-17; discussion S17-18 (1994); Talon D, Rouget C, Cailleaux V, Bailly P, Thouverez M, Barale F, Michel-Briand Y., "Nasal carriage of *Staphylococcus aureus* and cross-contamination in a surgical intensive care unit: efficacy of mupirocin ointment," *The Journal of Hospital Infection* 30:39-49 (1995); Wenisch C, Laferl H, Szell M, Smolle K H, Grisold A, Bertha G, Krause R., "A holistic approach to MRSA eradication in critically ill patients with MRSA pneumonia," *Infection* 34:148-154 (2006). However, the emergence of *S. aureus* mupirocin resistance has reduced the agent's efficacy both as a nasal decolonization agent and as a treatment option for skin and wound infections.

Low level mupirocin resistant *S. aureus* strains are commonly defined as exhibiting an MIC of 8 to ≤256 µg ml$^{-1}$ due to point mutations in the organism's native isoleucyl tRNA synthetase gene (ileRS) and develop rapidly in both the laboratory and clinical setting. See Lee A S, Gizard Y, Empel J, Bonetti E J, Harbarth S, Francois P., "Mupirocin-induced mutations in ileS in various genetic backgrounds of methicillin-resistant *Staphylococcus aureus*," *J Clin Microbiol* 52:3749-3754 (2014); High level mupirocin resistance (MIC of >512 mg/L) occurs less frequently and is attributable to the acquisition of a mobile genetic elements harboring either mupA, which codes for an alternate isolecyl tRNA synthetase, or the less-characterized mupB gene. See Fierobe L, Decre D, Muller C, Lucet J C, Marmuse J P, Mantz J, Desmonts J M., "Methicillin-resistant *Staphylococcus aureus* as a causative agent of postoperative intra-abdominal infection: relation to nasal colonization," *Clin Infect Dis* 29:1231-1238 (1999); Seah C, Alexander D C, Louie L, Simor A, Low D E, Longtin J, Melano R G., "MupB, a new high-level mupirocin resistance mechanism in *Staphylococcus aureus*," *Antimicrob Agents Chemother* 56:1916-1920 (2012). Indeed, a retrospective survey of methicillin resistant *S. aureus* (MRSA) nasal and blood isolates collected from 23 U.S. hospitals revealed that 3% and 5% isolates tested displayed high level mupirocin resistance, respectively, whereas single hospital low level mupirocin resistance ranges from 0% to 80%. See Hetem D J, Bonten M I, "Clinical relevance of mupirocin resistance in *Staphylococcus aureus*," *The Journal of Hospital Infection* 85:249-256 (2013). Thus, while mupirocin has proven an effective means of mediating *S. aureus* decolonization and reducing infection, mupriocin resistance has prompted renewed interest in developing alternative decolonization and wound infection treatment strategies.

*S. aureus* RNase P is an essential riboprotein complex consisting of RnpA and ribozyme rnpB that acts upstream of tRNA synthetases in the transfer RNA maturation pathway. More specifically RNase P catalyzes removal of the 5' leader sequences from precursor tRNA species creating mature tRNA substrates for tRNA synthetases including isoleucyl tRNA synthetase (the cellular target for mupirocin). Recognizing that two antimicrobials targeting independent steps of the same bacterial metabolic pathway can have combined antibacterial effects it has been hypothesized that combination therapies involving mixtures of RNase P inhibitors together with mupirocin would display increased antimicrobial efficacy and the potential to overcome mupirocin resistance. However, combining RNase P inhibitors with tRNA synthetase inhibitors for treating a bacterial infection or inhibiting bacterial growth has not consistently shown synergistic therapeutic effects in vitro, and so far none of the known combination therapies using the compounds from these two categories has shown in vivo synergistic effects in treating bacterial infections or inhibiting bacterial growth.

SUMMARY OF THE INVENTION

The present invention provides a composition having enhanced antimicrobial efficacy and effective for inhibiting, reducing or treating microbial infections such as bacterial infections, and/or for decolonizing a microbial organism and/or for destroying, disrupting, inhibiting or reducing bacterial biofilm formation. Described herein is the surprising and unexpected discovery that a composition comprising a combination of mupirocin and neomycin, when used to treat a microbial organism, demonstrates synergistic effect against a microbial, colonization or infection or biofilm formation.

In one aspect, the present invention provides a composition comprising mupirocin and neomycin. In one embodiment, the weight ratio between mupirocin and neomycin is from about 10:1 to about 1:10.

In one embodiment, the total concentration of mupirocin and neomycin in the composition of the present invention is about 50 weight percentage (wt. %), about 40 wt. %, about 30 wt. %, about 25 wt. %, about 20 wt. %, about 15 wt. %, about 10 wt. %, about 5 wt. %, about 3 wt. %, about 2 wt. %, about 1 wt. % per unit of the composition.

In one embodiment, the composition described herein is for topical administration to a subject. In one embodiment the subject has microbial infection. Preferably the microbial infection is characterized with microbial colonies or biofilm or biofilm formation. Preferably the microbial infection is a bacterial infection. In one embodiment, the bacteria infection is from Gram-positive or Gram-negative bacteria.

In another aspect, the present invention provides a topical formulation comprising mupirocin and neomycin and one or more pharmaceutically acceptable carriers or excipients. In one embodiment, the topical formulation comprises from about 0.001 wt. % to about 8 wt. % of mupirocin per unit of the formulation. In one embodiment, the topical formulation comprises from about 0.001 wt. % to about 8 wt. % of neomycin per unit of the formulation. In one embodiment, the topical formulation comprises from about 0.001 wt. % to about 8 wt. % of mupirocin and from about 0.001 wt. % to about 8 wt. % of neomycin per unit of the formulation.

In one embodiment, the topical formulation of the present invention comprises from about 0.001 wt. % to about 8 wt. % of mupirocin, from about 0.001 wt. % to about 8 wt. % of neomycin and about 10:1 to about 1:10 weight ratio between mupirocin and neomycin per unit of the formulation.

In one embodiment, the topical formulation of the present invention may take the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray or a pad.

In another aspect, the present invention provides a method of treating a microbial infection in a subject comprising administering to the subject separately, simultaneously or sequentially a therapeutically effective amount of mupirocin and neomycin.

In one embodiment, the present invention provides a method of decolonizing a microbial organism comprising contacting the microbial organism separately, simultaneously or sequentially with mupirocin and neomycin.

In one embodiment, the present invention provides a method of destroying or disrupting or inhibiting or reducing biofilm formation of a microbial organism comprising contacting the microbial organism separately, simultaneously or sequentially with mupirocin and neomycin.

According to any of the methods described herein, the biofilm formation is on a surface of a device. In one embodiment, the device is implanted catheters, prosthetic heart valves, cardiac pacemakers, contact lenses, cerebrospinal fluid shunts, joint replacements or intravascular lines. According to any of the methods described herein, the biofilm formation is on a surface of or in a tissue of a subject. In one embodiment, the biofilm formation is on a skin, eye, a mycous membrane, surface of cavity, etc.

DETAILED DESCRIPTION

Figure 1:
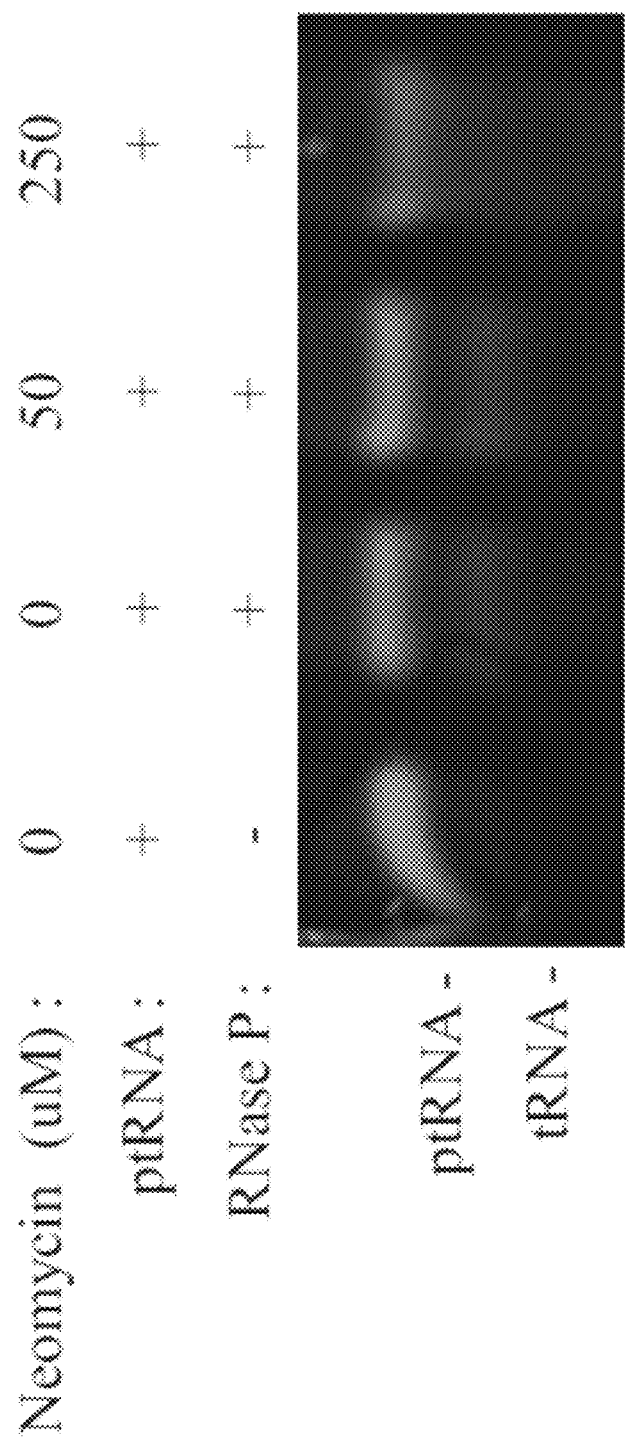
FIG. 1 shows that neomycin inhibits *S. aureus* RNase P's ability to catalyze the maturation of precursor tRNA$^{tyr}$ in vitro.

For purposes of interpreting this specification, the following definitions will apply and whenever appropriate, terms used in the singular will also include the plural and vice versa.

As used herein, the term "microbial organism" or "microbe," or "microbial," or "microorganism" refers to a domain (Bacteria) of prokaryotic round, spiral, or rod-shaped single-celled, multi-celled, or acelled microorganisms that may lack cell walls or are Gram-positive or Gram-negative or alteration thereof (i.e. *Mycobacterium*) if they have cell walls, that are often aggregated into colonies or motile by means of flagella, that typically live in soil, water, organic matter, or the bodies of plants and animals, that are usually autotrophic, saprophytic, or parasitic in nutrition, and that are noted for their biochemical effects and pathogenicity. The term is intended to encompass prokaryotic or eukaryotic cells or organisms having a microscopic size and includes bacteria, viruses, archaea and eubacteria of all species as well as eukaryotic microorganisms such as yeast and fungi. The term also includes cell cultures of any species that can be cultured for the production of a biochemical. In one non-limiting example, the activity of a microbial organism can be measured by calculating the log reduction in number of the microorganism.

As used herein, the term "microbial colonization" refers to the formation of compact population groups of the same type of microorganism, such as the colonies that develop when a microbial cell begins reproducing. The microbial colonization may or may not cause disease symptoms. Decolonization refers to a reduction in the number of microbial organisms present. When the microbial organisms are completely decolonized, the microbial organisms have been eradicated and are non-detectable.

As used herein, the term "biofilm" refers to matrix-enclosed microbial accretions to biological or non-biological surfaces in which microorganisms are dispersed and/or form colonies. The biofilm typically is made of polysaccharides and other macromolecules. Biofilm formation represents a protected mode of growth that allows cells to survive in hostile environments.

As used herein, the term "biofilm formation" is intended to include the formation, growth, and modification of the microbial colonies contained with biofilm structures, as well as the synthesis and maintenance of a polysaccharide matrix of the biofilm structures. Also within the scope of this term is formation of protein-based biofilms that do not secrete polysaccharide in the matrix but which comprise proteins that permit bacteria to form biofilm architecture.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces microbial colonization or infection. In one embodiment, the term refers to the amount that inhibits or reduces bacterial infection, or prevent or destroying the formation of bacterial biofilms. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. In the context of the present invention, a pharmaceutically acceptable carrier or excipient is preferably suitable for topical formulation. The term includes, but is not limited to, a solvent, a stabilizer, a solubilizer, a tonicity enhancing agent, a structure-forming agent, a suspending agent, a dispersing agent, a chelating agent, an emulsifying agent, an antifoaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. The use of such agents for the formulation of pharmaceutically active substances is well known in the art (see, for example, "Remington's Pharmaceutical Sciences", E. W. Martin, 18$^{th}$ Ed., 1990, Mack Publishing Co.: Easton, Pa., which is incorporated herein by reference in its entirety).

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder. The term "treating" or "treatment" also refers to a reduction in the severity of one or more symptoms by about 10%, about 20%, about 30%, about 40%, about 50%, about 60%, about 70%, about 80%, about 90% or about 100%.

As used herein, the term "topical administration" refers to the delivery to a subject by contacting the formulation directly to a surface or localized region of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition.

As used herein, the term "topical formulation" (synonymously, "topical composition") is used herein to refer to a pharmaceutical preparation intended for topical or local application to an afflicted region of a subject in need thereof, and includes such dosage forms as gel, cream, ointment, emulsion, suspension, solution, drops, lotion, paint, pessary, douche, suppository, troche, spray, sponge, film, or foam. Preferably, the topical formulation is in the form of a cream, a gel, or an ointment.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

As used herein, the term "about" refers to within 10%, preferably within 5%, and more preferably within 1% of a given value or range. Alternatively, the term "about" refers to within an acceptable standard error of the mean, when considered by one of ordinary skill in the art.

The present invention provides a composition having enhanced antimicrobial efficacy and effective for inhibiting, reducing or treating microbial infections such as bacterial infections, and/or for decolonizing a microbial organism and/or for destroying, disrupting, inhibiting or reducing bacterial biofilm formation. Described herein is the surprising and unexpected discovery that a composition comprising a combination of mupirocin and neomycin, when used to treat a microbial organism, demonstrates synergistic effect against a microbial, colonization or infection or biofilm formation. As used herein, the term "synergistic" refers to the effect obtained by combining compounds and/or agents that is greater than the effect obtained by the separate addition of each compound. The combination treatment of the present invention has shown a synergistic effect as measured by, for example, the extent of the response, the duration of response, the response rate, the stabilization rate, the duration of stabilization, the time to reduce or clear the infections, the time to eradicate the microorganisms, to that achievable on dosing one or other of the components of the combination treatment at its conventional dose. For example, the effect of the combination treatment of the present invention is synergistic because the combination treatment is therapeutically superior to the effect achievable with one component alone or the additive effect of the combination components acting separately. The superior effect can be improved reduction in drug resistance from the microbial organisms, the extent to which the microbial organisms are eradicated and become non-detectable by the combination treatment. Also for example, the effect of the combination treatment of the present invention is synergistic because it takes shorter time to kill the microorganisms and clear the infections. Also for example, the effect of the combination treatment of the present invention is synergistic because the combination treatment offers broader spectrum of antimicrobial activities than those with one component alone. Also for example, the effect of the combination treatment of the present invention is synergistic because one of the components in the composition described in this invention is dosed at its conventional dose and the other component(s) is/are dosed at a reduced dose and the therapeutic effect, as measured by, for example, the extent of the killing and/or inhibiting growth of the microorganisms such as bacteria, the time to kill and/or inhibit growth of the microorganisms such as bacteria, or the time to destroy or inhibit microbial colonies, or the time to disrupt or inhibit or reduce biofilm formation or growth, is equivalent to that achievable on dosing conventional amounts of the components of the combination treatment.

In one aspect, the present invention provides a composition comprising mupirocin and neomycin. In one embodiment, the weight ratio between mupirocin and neomycin is from about 10:1 to about 1:10. In one embodiment, the weight ratio between mupirocin and neomycin is from about 4:1 to about 1:4. In one embodiment, the weight ratio between mupirocin and neomycin is from about 2:1 to about 1:2. In one embodiment, the weight ratio between mupirocin and neomycin is about 1:1, about 1:2, about 1:3, about 1:4, about 1:5, about 2:1, about 3:1, about 4:1, or about 5:1. In one embodiment, the total concentration of mupirocin and neomycin in the composition of the present invention is from about 1 wt. % to about 50 wt. %. In one embodiment, the total concentration of mupirocin and neomycin in the composition of the present invention is about 50 weight percentage (wt. %), about 40 wt. %, about 30 wt. %, about 25 wt. %, about 20 wt. %, about 15 wt. %, about 10 wt. %, about 5 wt. %, about 3 wt. %, about 2 wt. %, about 1 wt. % per unit of the composition.

In one embodiment, the composition described herein is for topical administration to a subject. In one embodiment the subject has microbial infection or colonization by microbes. Preferably the microbial infection or colonization site is characterized with microbial colonies or biofilm or biofilm formation. Preferably the microbial infection is a bacterial infection. In one embodiment, the bacteria infection is from Gram-positive or Gram-negative bacteria. In one embodiment the bacterial infection is from one selected from *Staphylococcus* spp., e.g. *Staphylococcus aureus, Staphylococcus epidermidis; Enterococcus* spp., e.g. *Enterococcus faecalis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp.; *Streptococcus pyogenes; Listeria* spp.; *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptococcus* Group A or B, *Streptoccocus pneumoniae; Helicobacter* spp., e.g. *Helicobacter pylori; Neisseria* spp., e.g. *Neisseria gonorrhea, Neisseria meningitidis; Borrelia burgdorferi; Shigella* spp., e.g. *Shigella flexneri; Escherichia coli; Haemophilus* spp., e.g. *Haemophilus influenzae; Chlamydia* spp., e.g. *Chlamydia trachomatis, Chlamydia pneumoniae, Chlamydia psittaci; Francisella fularensis; Bacillus* spp., e.g. *Bacillus anthracis; Clostridia* spp., e.g. *Clostridium botulinum; Yersinia* spp., e.g. *Yersinia pestis; Treponema* spp.; *Burkholderia* spp.; e.g. *Burkholderia mallei* and *B pseudomallei*, or the combination thereof. Preferably the infection is from one of the ESKAPE pathogens including *Enterococcus* spp., e.g. *Enterococcus faecalis; Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof. Also in one embodiment, the bacteria are selected from *Acidothermus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtherias, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Finegoldia magna, Geobacillus kaustophilus, Geobacillus thermodenitrificans, Janibacter sp., Kineococcus radiotolerans, Lactobacillus fermentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides sp., Nocardia farcinica, Oceanobacillus iheyensis, Pelotomaculum the rmopropionicum, Rhodococcus sp., Saccharopolyspora erythraea,* coagulase-negative *Staphylococcus* species, *Staphylococcus aureus,* methicillin resistant *Staphylococcus aureus* (MRSA), *Staphylococcus epidermidis,* methicillin resistant *Staphylococcus epidermidis,* (MRSE), *Staphylococcus pseudintermedius, taphylococcus intermedius, Staphylococcus delphini, Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis,* or the combination thereof.

In another aspect, the present invention provides a topical formulation comprising mupirocin and neomycin and one or more pharmaceutically acceptable carriers or excipients. In one embodiment, the topical formulation comprises from about 0.001 wt. % to about 8 wt. % of mupirocin per unit of the formulation. In one embodiment, the topical formulation comprises from about 0.001 wt. % to about 8 wt. % of neomycin per unit of the formulation. In one embodiment, the topical formulation comprises from about 0.001 wt. % to about 8 wt. % of mupirocin and from about 0.001 wt. % to about 8 wt. % of neomycin per unit of the formulation.

In one embodiment, the topical formulation comprises from about 0.001 wt. % to about 4 wt. % of mupirocin and from about 0.001 wt. % to about 4 wt. % of neomycin per unit of the formulation. In one embodiment, the topical formulation comprises from about 0.015 wt. % to about 2 wt. % of mupirocin and from about 0.015 wt. % to about 2 wt. % of neomycin per unit of the formulation. In one embodiment, the topical formulation comprises one selected from about 0.25 wt. %, about 1 wt. %, or about 2 wt. % of mupirocin and one selected from about 0.25 wt. %, about 0.5 wt. %, or about 1 wt. % of neomycin per unit of the formulation.

In one embodiment, the topical formulation of the present invention comprises from about 0.001 wt. % to about 8 wt. % of mupirocin, from about 0.001 wt. % to about 8 wt. % of neomycin and about 10:1 to about 1:10 weight ratio between mupirocin and neomycin per unit of the formulation. In one embodiment, the topical formulation of the present invention comprises from about 0.001 wt. % to about 4 wt. % of mupirocin, from about 0.001 wt. % to about 4 wt. % of neomycin and from about 4:1 to about 1:4 weight ratio between mupirocin and neomycin per unit of the formulation. In one embodiment, the topical formulation of the present invention comprises from about 0.015 wt. % to about 0.5 wt. % of mupirocin, from about 0.015 wt. % to about 0.5 wt. % of neomycin and from about 2:1 to about 1:2 weight ratio between mupirocin and neomycin per unit of the formulation.

In one embodiment, the topical formulation of the present invention may take the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray or a pad.

The topical formulation of the present invention comprises one or more pharmaceutically acceptable carrier. Examples of the pharmaceutically acceptable carriers that are usable in the context of the present invention include carrier materials such as a solvent, a stabilizer, a solubilizer, a filler, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof.

Examples of solvents are water or purified water, alcohols (e.g., ethanol, benzyl alcohol), vegetable, marine and mineral oils, polyethylene glycols, propylene glycols, glycerol, and liquid polyalkylsiloxanes.

Inert diluents or fillers may be sucrose, sorbitol, sugar, mannitol, microcrystalline cellulose, starches, calcium carbonate, sodium chloride, lactose, calcium phosphate, calcium sulfate, or sodium phosphate.

Examples of buffering agents include citric acid, acetic acid, lactic acid, hydrogenophosphoric acid, diethylamine, sodium hydroxide and tromethane (/.e., tris(hydroxymethyl) aminomethane hydrochloride).

Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans.

Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a topical composition of the invention to prevent microbial contamination that can affect the stability of the formulation and/or cause infection in the patient. Suitable examples of preservatives include parabens (such as methyl, ethyl, propyl, /p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol.

Examples of chelating agents include sodium EDTA and citric acid.

Examples of gel bases or viscosity-increasing agents are liquid paraffin, polyethylene, fatty oils, colloidal silica or aluminum, glycerol, propylene glycol, propylene carbonate, carboxyvinyl polymers, magnesium-aluminum silicates, hydrophilic polymers (such as, for example, starch or cellulose derivatives), water-swellable hydrocolloids, carragenans, hyaluronates, alginates, and acrylates.

Ointment bases suitable for use in the compositions of the present invention may be hydrophobic or hydrophilic, and include paraffin, lanolin, liquid polyalkylsiloxanes, cetanol, cetyl palmitate, vegetal oils, sorbitan esters of fatty acids, polyethylene glycols, and condensation products between sorbitan esters of fatty acids, ethylene oxide (e.g., polyoxyethylene sorbitan monooleate), polysorbates, white petrolatum and white wax.

Examples of humectants are ethanol, isopropanol glycerin, propylene glycol, sorbitol, lactic acid, and urea. Suitable emollients include cholesterol and glycerol.

Examples of skin protectants include vitamin E, allatoin, glycerin, zinc oxide, vitamins, and sunscreen agents.

Thickening agents are generally used to increase viscosity and improve bioadhesive properties of pharmaceutical or cosmetic compositions. Examples of thickening agents include, but are not limited to, celluloses, polyethylene glycol, polyethylene oxide, naturally occurring gums, gelatin, karaya, pectin, alginic acid, povidone, and Carbopol® polymers. Particularly interesting are thickening agents with thixotropic properties (i.e., agents whose viscosity is decreased by shaking or stirring). The presence of such an agent in a composition allows the viscosity of the composition to be reduced at the time of administration to facilitate its application to the skin and, to increase after application so that the composition remains at the site of administration.

Bioadhesive polymers are useful to hydrate the skin and enhance its permeability. Bioadhesive polymers can also function as thickening agents. Examples of bioadhesive polymers include, but are not limited to, pectin, alginic acid, chitosan, polysorbates, poly(ethyleneglycol), oligosaccharides and polysaccharides, cellulose esters and cellulose ethers, and modified cellulose polymers.

Permeation enhancing agents are vehicles containing specific agents that affect the delivery of active components through the skin. Permeation enhancing agents are generally divided into two classes: solvents and surface active compounds (amphiphilic molecules). Examples of solvent permeation enhancing agents include alcohols (e.g., ethyl alcohol, isopropyl alcohol), dimethyl formamide, dimethyl acetamide, dimethyl sulfoxide, 1-dodecylazocyloheptan-2-one, N-decyl-methylsulfoxide, lactic acid, N,N-diethyl-m-toluamide, N-methyl pyrrolidone, nonane, oleic acid, petrolatum, polyethylene glycol, propylene glycol, salicylic acid, urea, terpenes, and trichloroethanol. Surfactant permeation enhancing agents may be nonionic, amphoteric, cationic, or zwitterionic. Suitable nonioinic surfactants include poly(oxyethylene)-poly(oxypropylene) block copolymers, commercially known as poloxamers; ethoxylated hydrogenated castor oils; polysorbates, such as Tween 20 or Tween 80. Amphoteric surfactants include quaternized imidazole derivatives, cationic surfactants include cetypyridinium chloride, and zwitterionic surfactants include the betaines and sulfobetaines. Other examples of suitable permeation enhancers include pentadecalactone, 2-pyrrolidine, 1-dodecal-azacycloheptane-2-one, calcium thioglycolate, hexanol, derivatives of 1,3-dioxanes (i.e., 1,3-dioxacyclohexanes) and 1,3-dioxalanes (i.e., 1,3-dioxacyclopentanes), 1-N-dodecyl-2-pyrrolidone-5-carboxylic acid, 2-pentyl-2-oxo-pyrrolidineacetic acid, 2-dodecyl-2-oxo-1-pyrrolidineacetic acid, and 1-azacycloheptan-2-one-2-dodecylacetic acid among others.

In another aspect, the present invention provides a method of treating a microbial infection in a subject comprising administering to the subject separately, simultaneously or sequentially a therapeutically effective amount of mupirocin and neomycin. In one embodiment, the method comprises administering to the subject a therapeutically effective amount of a composition comprising mupirocin and neomycin described herein. In one embodiment, the method comprises administering to the subject a therapeutically effective amount of a topical formulation comprising mupirocin and neomycin described herein and one or more pharmaceutically acceptable carriers or excipients, wherein the topical formulation and the pharmaceutically acceptable carriers or excipients are defined herein throughout the specification. In one embodiment, the infection is a topical infection. The topical infection is an infection on a surface or localized region of a subject including skin, eye, a mucous membrane, a surface of cavity, etc. In one embodiment, the topical infection is the infection on the skin. In one embodiment, the topical infection is in the form of wound, ulcer and lesion. According to any of the methods described herein, the microbial organism is a bacterium. Preferably the bacterium is one selected from the ESKAPE pathogens including *Enterococcus* spp., e.g. *Enterococcus faecalis, Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof.

In one embodiment, the present invention provides a method of decolonizing a microbial organism comprising contacting the microbial organism separately, simultaneously or sequentially with mupirocin and neomycin. In one embodiment, the method comprises contacting the microbial organism with a composition comprising mupirocin and neomycin described herein. In one embodiment, the method comprises contacting the microbial organism with a topical formulation comprising mupirocin and neomycin described herein and one or more pharmaceutically acceptable carriers or excipients, wherein the topical formulation and the pharmaceutically acceptable carriers or excipients are defined herein throughout the specification. According to any of the methods describes herein, the microbial organism is a bacterium. Preferably the bacterium is one selected from the ESKAPE pathogens including *Enterococcus* spp., e.g. *Enterococcus faecalis; Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof. According to any of the methods described herein, the biofilm formation is on a surface of a device. In one embodiment, the device is implanted catheters, prosthetic heart valves, cardiac pacemakers, contact lenses, cerebrospinal fluid shunts, joint replacements or intravascular lines. According to any of the methods described herein, the biofilm formation is on a surface of or in a tissue of a subject. In one embodiment, the biofilm formation is on a skin, eye, a mycous membrane, surface of cavity, etc.

In one embodiment, the present invention provides a method of destroying or disrupting or inhibiting or reducing biofilm formation of a microbial organism comprising contacting the microbial organism separately, simultaneously or sequentially with mupirocine and neomycin. In one embodiment, the method comprises contacting the microbial organism with a composition comprising mupirocin and neomycin described herein. In one embodiment, the method comprises contacting the microbial organism with a topical formulation comprising mupirocin and neomycin described herein and one or more pharmaceutically acceptable carriers or excipients, wherein the pharmaceutically acceptable carriers or excipients are defined herein throughout the specification. According to any of the methods describes herein, the microbial organism is a bacterium. Preferably the bacterium is one selected from the ESKAPE pathogens including *Enterococcus* spp., e.g. *Enterococcus faecalis*, *Staphylococcus* spp., e.g. *Staphylococcus aureus*, *Staphylococcus epidermidis*; *Klebsiella* spp., e.g. *Klebsiella pneumoniae*; *Acinetobacter* spp., e.g. *Acinetobacter baumannii*; *Pseudomonas* spp., e.g. *Pseudomonas aeruginosa*; *Enterobacter* spp., or the combination thereof. According to any of the methods described herein, the biofilm formation is on a surface of a device. In one embodiment, the device is implanted catheters, prosthetic heart valves, cardiac pacemakers, contact lenses, cerebrospinal fluid shunts, joint replacements or intravascular lines. According to any of the methods described herein, the biofilm formation is on a surface of or in a tissue of a subject. In one embodiment, the biofilm formation is on a skin, eye, a mycous membrane, surface of cavity, etc.

Accordingly the present invention provides the use of mupirocin and neomycin for treating a microbial infection, or for decolonizing a microbial organism, or for destroying or disrupting or inhibiting or reducing biofilm formation of a microbial organism.

Accordingly the present invention provides the use of a combination comprising mupirocin and neomycin for treating a microbial infection, or for decolonizing a microbial organism, or for destroying or disrupting or inhibiting or reducing biofilm formation of a microbial organism.

Accordingly the present invention provides the use of a topical formulation for treating a microbial infection, or for decolonizing a microbial organism, or for destroying or disrupting or inhibiting or reducing biofilm formation of a microbial organism, said topical formulation comprises mupirocin and neomycin and one or more pharmaceutically acceptable carriers or excipients.

The combination therapy of the present invention may be performed alone or in conjunction with another therapy. For example, the combination therapy of the present invention may be used in conjunction with a disinfectant, antiseptic, antibiotic, or biocide on a surface such as medical devices and indwelling devices including stents, catheters, peritoneal dialysis tubing, draining devices, joint prostheses, dental implants and the like.

By way of examples below, the present invention provides a synergistic combination therapy comprising mupirocin and neomycin that can be administered topically for the treatment of a microbial colonized surface or infection. Reference is now made to the following examples, which together with the above descriptions illustrate some embodiments of the invention in a non-limiting manner.

EXAMPLES

Introduction

*Staphylococcus aureus* has been designated as one of the six ESKAPE bacterial pathogens of greatest U.S. healthcare concern. See Rice L B. 2008. Federal funding for the study of antimicrobial resistance in nosocomial pathogens: no ESKAPE. J Infect Dis 197:1079-1081. The organism is a predominant cause of nosocomial- and community-associated bacterial infections and has developed resistance to all currently available antibiotics. See Pendleton J N, Gorman S P, Gilmore B F. 2013. Clinical relevance of the ESKAPE pathogens. Expert review of anti-infective therapy 11:297-308. *S. aureus* annual U.S. mortality rates have already surpassed that of HIV/AIDS and are likely to worsen given the outright elimination, downsizing and/or redirection of antimicrobial programs targeting other organisms by most pharmaceutical companies. See Klevens R M, Morrison M A, Nadle J, Petit S, Gershman K, Ray S, Harrison L H, Lynfield R, Dumyati G, Townes J M, Craig A S, Zell E R, Fosheim G E, McDougal L K, Carey R B, Fridkin S K. 2007. Invasive methicillin-resistant *Staphylococcus aureus* infections in the United States. JAMA: the journal of the American Medical Association 298:1763-1771; Projan S J, Shlaes D M. 2004. Antibacterial drug discovery: is it all downhill from here? Clinical microbiology and infection: the official publication of the European Society of Clinical Microbiology and Infectious Diseases 10 Suppl 4:18-22. Simply put, new strategies are urgently needed for the prevention and treatment of staphylococcal infections.

The anterior nares of humans is a principle ecological niche for *S. aureus* and nasal carriage is a recognized risk factor for staphylococcal disease, particularly among patient populations undergoing surgical procedures, hemodialysis, or requiring long term intensive care unit stays [reviewed in Kluytmans J, van Belkum A, Verbrugh H. 1997. Nasal carriage of *Staphylococcus aureus*: epidemiology, underlying mechanisms, and associated risks. Clin Microbiol Rev 10:505-520.]. Studies indicate that *S. aureus* nasal decolonization reduces colonization of other body sites and the risk of transmission and subsequent infection. Consequently, infection control practices routinely include nasal decolonization procedures as a means to prevent *S. aureus* infection and ultimately reliance on antibiotic intervention of staphylococcal disease.

*S. aureus* RNase P is an essential riboprotein complex consisting of RnpA and ribozyme rnpB that acts upstream of tRNA synthetases in the transfer RNA maturation pathway. More specifically RNase P catalyzes removal of the 5' leader sequences from precursor tRNA species creating mature tRNA substrates for tRNA synthetases including isoleucyl tRNA synthetase (the cellular target for mupirocin). Recognizing that two antimicrobials targeting independent steps the same bacterial metabolic pathway can have combined antibacterial effects it has been previously hypothesized that combination therapies involving mixtures of RNase P inhibitors together with mupirocin would display increased antimicrobial efficacy and the potential to overcome mupirocin resistance. In support of that prediction, RNPA2000, a small molecule inhibitor of *S. aureus* RNase P activity, was shown to display synergistic activity with mupirocin but not other antibiotics tested during laboratory growth conditions. Unfortunately, as shown below, RNPA2000 loses antimicrobial properties in the host setting and does not display synergism with mupirocin in host models of colonization and infection. Thus, while RNase P inhibitors may confer synergistic activity during laboratory conditions, it is not obvious which RNase P inhibitors, if any, will confer synergistic effects in the host if, for example, bacteria do not require RNase P function for survival during colonization, infection, or in the host setting.

Described herein are the results of a screen of a Food and Drug Administration (F.D.A.) approved drug library for agents that potentiate the antimicrobial properties of mupirocin toward *S. aureus*. The antibiotic neomycin sulfate, which is approved for topical use and previously shown to inhibit *Escherichia coli* RNase P was among the three hits identified. In vitro assays revealed that neomycin also inhibits S. aureus RNase P function, confers an additive antimicrobial advantage to mupirocin and the combination could be effectively formulated in topical format. Animal studies demonstrated that the combination of neomycin+mupirocin topical application reduced S. aureus bacterial burden in murine models of nasal colonization and wound site infections. Further, combination therapy improved upon the effects of either agent alone and was effective in the treatment of contemporary methicillin susceptible, methicillin resistant, and high level mupirocin resistant S. aureus strains.

Example 1

Materials and Methods

Bacterial Strains and Animals. All bacterial studies were performed with Staphylococcus aureus strain UAMS-1, a well-characterized methicillin susceptible clinical isolate commonly used to study the organism's biofilm formation and colonization properties, USA300, a methicillin resistant community-acquired clinical isolate or BAA-1708 a high level mupirocin resistant strain containing mupA obtained from the American Type Culture Collection (Manassas, Va.). See Gillaspy A F, Hickmon S G, Skinner R A, Thomas J R, Nelson C L, Smeltzer M S. 1995. Role of the accessory gene regulator (agr) in pathogenesis of staphylococcal osteomyelitis. Infect Immun 63:3373-3380; McDougal L K, Steward C D, Killgore G E, Chaitram J M, McAllister S K, Tenover F C. 2003. Pulsed-field gel electrophoresis typing of oxacillin-resistant Staphylococcus aureus isolates from the United States: establishing a national database. J Clin Microbiol 41:5113-5120. Unless otherwise indicated, strains were grown overnight in tryptic soy broth (TSB) then used to inoculate a fresh (1:100 dilution) media, grown to early exponential phase ($1\times10^8$ CFU/mL) and processed as described below. Female Balb/C mice 4-6 weeks of age were obtained from Charles River (Wilmington Mass.) and housed according to approved University of Rochester Medical Center Council on Animal Research (UCAR) protocols.

Preparation of Test Articles. Polyethylene glycol (PEG) ointment-base was prepared by mixing PEG 400 (70% w/v) with PEG 3350 (30% w/v) as described by the United States Pharmacopeia and The National Formulary (USP 24-NF 19). Mupirocin (AppliChem, Chicago Ill.; A47180005) and neomycin (Sigma, St. Louis Mo.; N6386) were suspended in 250 µL of dimethyl sulfoxide (DMSO) to create working concentrations of 100 mg and 50 mg, respectively. Mixtures were then added directly to 5 g of PEG ointment pre-liquified by heating at 60° C. for 30 min to create 2% mupirocin, 1% neomycin suspensions then cooled to room temperature. The same procedure was used to create DMSO vehicle control and 2% mupirocin/1% neomycin PEG mixtures by adding a combination of 100 mg mupirocin and 50 mg neomycin in a total 250 µL DMSO.

Screen of Selleck Library. Members of the Selleck Library of Food and Drug Association approved drugs (Selleck Chemicals, Houston Tex., L1300) were screened for agents that potentiate the antimicrobial activity of mupirocin toward S. aureus strain UAMS-1. To do so, $1\times10^5$ colony forming units of UAMS-1 were added to individual wells of a 96-well microtiter plate, mixed with 0.03 µg/mL mupirocin (0.5× minimum inhibitory concentration) and 50 µM of test agent in Mueller Hinton broth (MHB; 100 µL total well volume). Microtiter plates were incubated at 37° C. for 16 hr, and individual wells were inspected for growth. Wells lacking growth were considered to represent agents that either potentiated the antimicrobial properties of mupirocin or mupirocin-independent antimicrobial microbial properties. All drugs that resulted in no growth were confirmed in duplicate and were plated without mupirocin to measure their inherent antimicrobial activity.

RNase P ptRNA Processing Assay. S. aureus RNase P activity assays were performed as previously described. See Eidem T M, Lounsbury N, Emery J F, Bulger J, Smith A, Abou-Gharbia M, Childers W, Dunman P M. 2015. Small-molecule inhibitors of Staphylococcus aureus RnpA-mediated RNA turnover and tRNA processing. Antimicrob Agents Chemother 59:2016-2028. Briefly, RNase P was first reconstituted by mixing an equimolar ratio of denatured rnpB and RnpA for 15 min at 37° C. then added (5 pmol) to 10 pmol of ptRNA$^{Tyr}$, and increasing concentrations of the indicated concentration of neomycin or the known RNase P inhibitor, RNPA2000 in a total volume of 20 µl. Mixtures were incubated for 5 min at 37° C., stopped by adding 20 µL of 2×RNA loading dye (95% formamide, 0.025% SDS, 0.025% bromophenol blue, 0.025% xylene cyanol FF, 0.5 mM EDTA), and 30 µL of each sample was electrophoresed in a 7M urea—8% polyacrylamide gel and stained with ethidium bromide (0.5 µg/mL). A FluorChem 5500 imaging system was used to visualize RNA products and quantified using ImageJ software (National Institutes of Health, Bethesda Md.). The percent RNase P activity was then calculated using the following equation: test compound tRNA$^{Tyr}$ signal/mock tRNA$^{Tyr}$ signal.

Antimicrobial Susceptibility Testing. Minimum inhibitory concentration (MIC) was tested in accordance with the Clinical and Laboratory Standards Institute (CLSI) guidelines. Briefly, $1\times10^5$ CFU of the indicated S. aureus strain was added to individual wells of a microtiter plate containing 88 µL of MHB media and two-fold increasing concentrations of mupirocin or test agent (0-128 µg ml$^{-1}$). Plates were incubated for 16 hr at 37° C. and wells were visually inspected for growth. The lowest concentration of mupirocin or test agent that inhibited S. aureus growth was considered to be the minimum inhibitory concentration. Fractional inhibitory concentration index (FIC) testing was performed to measure interactions between mupirocin and neomycin, as previously described. See Odds F C. 2003. Synergy, antagonism, and what the chequerboard puts between them. The Journal of antimicrobial chemotherapy 52:1. Briefly, in checkerboard format each row of the plate contained increasing concentrations of mupirocin (2-fold increments; 0-0.5 µg/mL), whereas each column contained increasing concentrations of neomycin (2-fold increments; 0-32 µg/mL). To every well (100 µl total volume) MHB containing $3\times10^5$ CFU of S. aureus strain UAMS-1 was added and the plate was incubated at 37° C. overnight (16-20 hr). The FIC was determined using the following formula: (MIC of Drug A in Combination/MIC of Drug A Alone)+(MIC of Drug B in Combination/MIC of Drug B Alone)=FIC. A synergistic interaction was defined as an FIC value≤0.5, additive as FIC value 0.5-1.0, no interaction as an FIC of 1-4, or an antagonistic interaction FIC>4.

In vitro Ointment Antimicrobial Testing. Antimicrobial zones of inhibition where measured for PEG ointment compilations using the indicated S. aureus strains. To do so, 100 µL of $1\times10^8$ CFU ml$^{-1}$ of S. aureus was spread on TSA plates. Plates were dried for 10 min and 40 µL of ointment was pipetted onto the center of the plate. Plates were incubated at 37° C. for 16 hr and zones of bacterial clearance were measured using ImageJ software (NIH).

Nasal Colonization and Treatment of Mice. Ointments were evaluated for in vivo antimicrobial activity using a *S. aureus* nasal colonization model as previously described, but with modifications. See Kiser K B, Cantey-Kiser J M, Lee J C. 1999. Development and characterization of a *Staphylococcus aureus* nasal colonization model in mice. Infect Immun 67:5001-5006. The nostrils of awake mice were inoculated with $1 \times 10^7$ of the indicated *S. aureus* strain by pipetting 10 µL of culture directly into the nostrils and confirmed by the visualization of air bubbles appearing as the mouse breathed in and out. Mice nostrils were then treated with 10 µL PEG ointment (brought to 55° C. in a heat block to liquefy) containing either vehicle alone or the indicated antibiotic 45 min post inoculation and treatments were repeated every 8 hr for three days. Mice were then euthanized via $CO_2$ asphyxiation and cervical dislocation, as per UCAR approved methodology. The full nares from the back of the soft palate to the tip of the nostrils was collected by gross dissection and placed in microcentrifuge tubes containing 1 mL of freshly made PBS. Samples were homogenized for five minutes, serially diluted, and plated on Mannitol Salt agar (MSA, ThermoScientific, Waltham Mass.; R453902). Plates were incubated for 16 hr and the number of *S. aureus* were enumerated.

Dermal Wound Model of Infection and Treatment of Mice. The effects of ointment compilations were evaluated for in vivo antimicrobial activity using a *S. aureus* dermal wound model, but with modifications. See Guthrie K M, Agarwal A, Tackes D S, Johnson K W, Abbott N L, Murphy C J, Czuprynski C J, Kierski P R, Schurr M J, McAnulty J F. 2012. Antibacterial efficacy of silver-impregnated polyelectrolyte multilayers immobilized on a biological dressing in a murine wound infection model. Annals of surgery 256:371-377. Mice were anesthetized by intraperitoneal injection with a mixture of 100 mg ml$^{-1}$ Ketamine (Hospira Inc., Lake Forest Ill.) and 20 mg ml$^{-1}$ Xylazine (Lloyd Laboratories, Shenandoah Iowa) in NaCl at five µl per 1 g body weight. Pain relief in the form of 20 µL 0.5% Sensorcaine (APP Pharmaceuticals, Schaumburg, Ill.) was administered prior to dermal wounding. The dorsal mid-section of the mouse was shaved and cleaned with a series of betadine scrub (FisherScientific), povidone-iodine pads (Professional Disposables International Inc; Orangeburg, N.Y.) and isopropyl alcohol pads (FisherScientfic) for a total contact time of two minutes. A single wound was created in this sterile field on the mouse with a 6 mm biopsy punch (FisherScientific) to remove only the dermal layer and not disrupt the underlying musculature. The wounds of the mice were inoculated with $1 \times 10^7$ of the indicated *S. aureus* strain by pipetting 10 µL of culture directly onto the wound. Mice were then treated with ointment compilations (50 µL) containing either vehicle alone, or indicated antibiotics 45 min post inoculation; treatments were repeated every 12 hr for three days. Mice were then euthanized via $CO_2$ asphyxiation and cervical dislocation, as per UCAR approved methodology, the wound and underlying muscle was excised with an 8 mm biopsy punch (PDI) and placed in microcentrifuge tubes containing 1 mL of freshly made PBS. Samples were homogenized for five minutes, serially diluted, and plated on MSA. Plates were incubated for 16 hr and the number of *S. aureus* was enumerated.

In vivo Toxicity Testing. Ointment toxicity was tested in a modified dermal wound model. Mice in groups of three per indicated treatment group were wounded as described above without inoculation of the wound with *S. aureus*. The wound was treated with vehicle, 2% mupirocin, 1% neomycin, or 2% mupirocin plus 1% neomycin combination ointments twice daily for 14 days. Mice were weighed, assessed for grooming and alertness, and images of the wound were obtained daily to measure wound contraction using Image J (NIH). Wound contraction was calculated as percentage of wound area reduction using the formula: $WCd=(1-WAd/WA0) \times 100$, where WC is wound contraction, WA is wound area, d is day, and 0 indicates initial day. See Amegbor K, Metowogo K, Eklu-Gadegbeku K, Agbonon A, Aklikokou K A, Napo-Koura G, Gbeassor M. 2012. Preliminary evaluation of the wound healing effect of Vitex doniana sweet (Verbenaceae) in mice. African journal of traditional, complementary, and alternative medicines: AJTCAM/African Networks on Ethnomedicines 9:584-590.

Example 2

Agents that Potentiate the Antimicrobial Activity of Mupirocin

Members of the Selleck library of 853 FDA approved drugs were screened for agents that potentiate the activity of mupirocin. To do so, *S. aureus* strain UAMS-1 was inoculated into individual wells of a microtiter plate containing 0.25× the strain's mupirocin minimum inhibitory concentration (MIC; 0.3 µg ml$^{-1}$) and 50 µM of library material. A total of 108 library members (12.6%) inhibited bacterial growth, suggesting that they may represent agents that potentiate the antimicrobial activity of mupirocin, exhibit mupirocin-independent antimicrobial activity, or both. To distinguish between these possibilities, increasing concentrations of each compound were retested for antimicrobial activity in medium lacking or containing 0.25× the strain's mupirocin MIC. 105 of the 108 compounds (97.2%) evaluated displayed similar antimicrobial activity regardless of whether mupriocin was present. Conversely, the antimicrobial activity of Nitazoxanide, Nitrofurazone, and Neomycin sulfate, increased in the presence of mupirocin. Indeed, fractional inhibitory concentration index (FIC) measures revealed an additive effect with each agent (FTC's=0.75) when combined with mupirocin indicating that they are antimicrobial agents that also have the capacity to potentiate the activity of mupirocin, perhaps by inhibiting RNase P (Table 1).

TABLE 1

Selleck Library Members with Mupirocin-Associated Improved Activity

| Drug | MIC (µg ml$^{-1}$) | | Fractional Inhibitory Concentration Index |
|---|---|---|---|
| | (−) Mup. | (+) Mup. | |
| Nitazoxanide | 16 | 8 | 0.75 |
| Nitrofurazone | 16 | 8 | 0.75 |
| Neomycin sulfate | 0.5 | 0.25 | 0.75 |

Example 3

Neomycin Inhibits *S. aureus* RNase P In Vitro Activity

Aminoglycoside antibiotics, such has neomycin, contain a central deoxystreptamine ring decorated with amino-sugar modifications and act by binding to the major groove of the 16S rRNA to disrupt the fidelity of tRNA selection and block protein translation. More recent studies have revealed that aminoglycosides can also bind and affect the function of mRNAs, tRNAs, and catalytic RNAs. See Mikkelsen N E, Brannvall M, Virtanen A, Kirsebom L A. 1999. Inhibition of RNase P RNA cleavage by aminoglycosides. Proc Natl Acad Sci USA 96:6155-6160; Mikkelsen N E, Johansson K, Virtanen A, Kirsebom L A. 2001. Aminoglycoside binding displaces a divalent metal ion in a tRNA-neomycin B complex. Nature structural biology 8:510-514; Tok J B, Cho J, Rando R R. 1999. Aminoglycoside antibiotics are able to specifically bind the 5'-untranslated region of thymidylate synthase messenger RNA. Biochemistry 38:199-206; von Ahsen U, Davies J, Schroeder R. 1992. Non-competitive inhibition of group I intron RNA self-splicing by aminoglycoside antibiotics. Journal of molecular biology 226:935-941. In that regard, neomycin B and/or derivatives have been shown to bind to the rnpB component of RNase P and/or precursor tRNA molecules in a manner that inhibits *Escherichia coli, Neisseria gonorrhoeae, Porphyromas gingivalis, Streptococcus pneumoniae* and *Bacillus subtilis* RNase P function. See Eubank T D, Biswas R, Jovanovic M, Litovchick A, Lapidot A, Gopalan V. 2002. Inhibition of bacterial RNase P by aminoglycoside-arginine conjugates. FEBS letters 511:107-112; Liu X, Chen Y, Fierke C A. 2014. A real-time fluorescence polarization activity assay to screen for inhibitors of bacterial ribonuclease P. Nucleic acids research 42:e159. Accordingly, it was evaluated whether neomycin also inhibits *S. aureus* RNase P activity in an in vitro precursor tRNA processing assay. As shown in FIG. 1., results revealed that high concentrations (250 μM) of neomycin inhibit *S. aureus* RNase P's ability to catalyze the maturation of precursor tRNA$^{Tyr}$ during in vitro conditions, suggesting that the agent's ability to potentiate mupirocin may, in part, be mediated by its ability to inhibit RNase P activity.

Example 4

Antimicrobial Effects of Mupirocin and Neomycin Combination in Ointment Formation As noted earlier mupirocin ointment is losing efficacy as a staphylococcal decolonization and wound treatment agent due to the emergence of mupirocin resistance and new options are needed for the prevention and treatment of *S. aureus* infection. Given that neomycin improves the antimicrobial potency of mupirocin and the two antibiotics have differing mechanisms of action, it was examined whether combination ointments containing both agents may have improved antimicrobial properties in comparison to either agent alone. Further, combination therapy would overcome mupirocin resistance, and incorporation of neomycin, which predominantly affects Gram-negative species, into mupirocin ointments would offer the potential of improve spectrum of antimicrobial activity which may prove beneficial in terms of reducing the incidence of secondary infections or polymicrobial wound infections. As a first test of these possibilities, the antimicrobial performance of each agent in polyethylene glycol (PEG) based-ointment was measured.

Figures 2A, 2B, 2C, 2D, 2E:
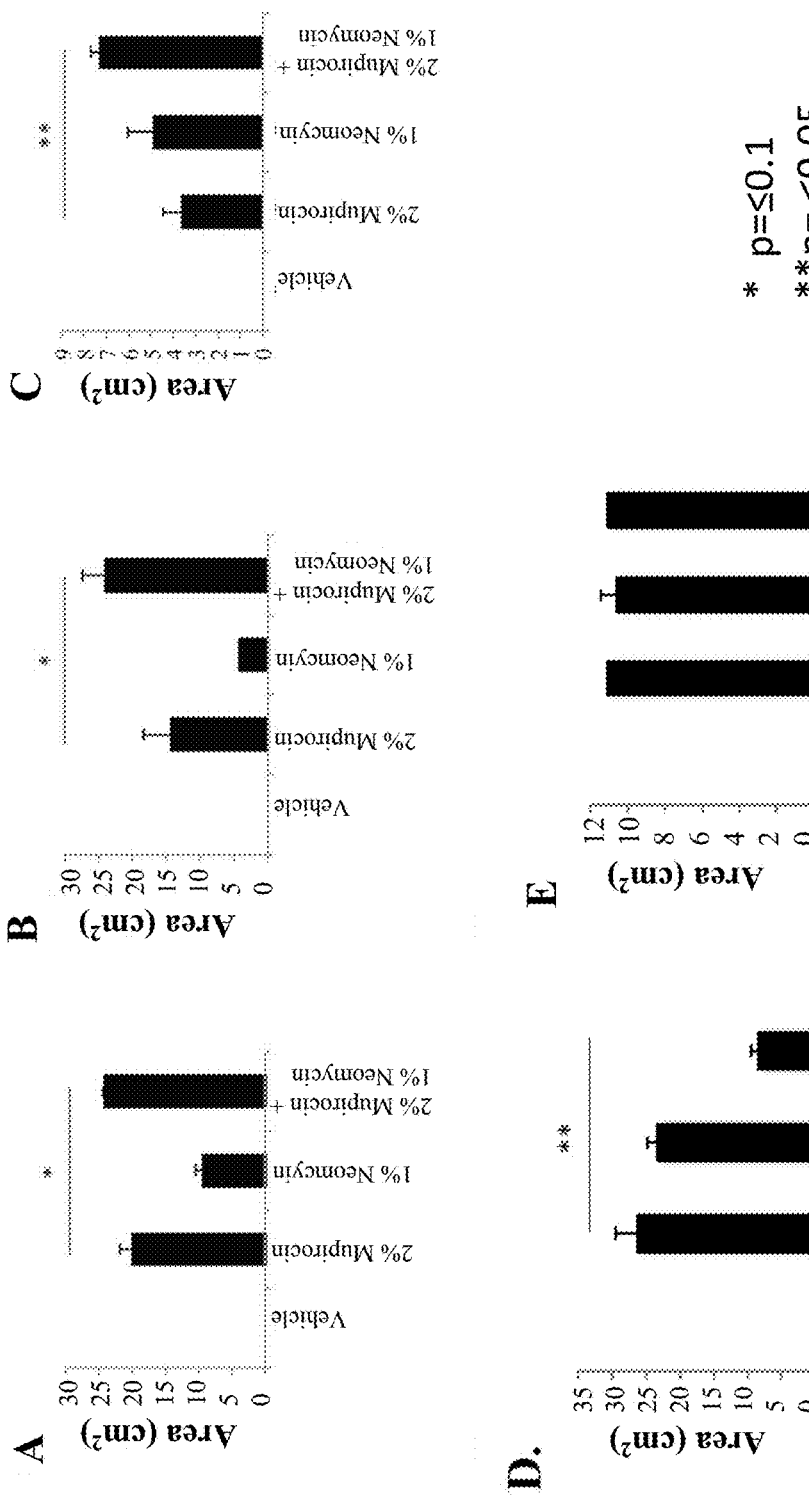
FIGS. 2A-2C show that the ointment formulation does not antagonize the antimicrobial inhibition of either mupirocin or neomycin and that the mupirocin and neomycin combination in ointment formulation has improved antimicrobial clearance.
FIGS. 2D and 2E show that combinations of mupirocin and other antibiotics exhibit antagonistic or no improved antimicrobial clearance in ointment formulation.

Plate assays were initially used to monitor the antimicrobial effects of PEG-based ointments containing either DMSO (vehicle), 2% mupirocin, 1% neomycin, or combination (2% mupirocin+1% neomycin) toward *S. aureus* strain UAMS-1, a neomycin and mupirocin susceptible clinical isolate. As shown in FIG. 2A., measurements of each treatment's zone of inhibition revealed that while vehicle alone did not affect the organism's growth, both antibiotics, alone and in combination, produced zones of growth inhibition, suggesting that the ointment formulation did not antagonize the antimicrobial properties of either agent. Two percent mupirocin generated a zone of inhibition 21.1 (±2) cm$^2$, whereas 1% neomycin exhibited an average zone of clearance of 9.7 (±1) cm$^2$. The combination of 2% mupirocin and 1% neomycin displayed the greatest zone of inhibition (29.9 (±0.25) cm$^2$) that was considered statistically improved over that of mupirocin alone, which could be attributed to either the additive effects of the specific antibiotic combination or merely reflect an overall increase in active antimicrobial ingredients. However, similar improvements in antimicrobial clearance were not observed in tests of 2% mupirocin in combination with 1% vancomycin (FIG. 2D) or oxacillin (FIG. 2E), which showed antagonistic and no improvement in combination, respectively. These results indicate that the additive effects of mupirocin+neomycin combination observed in liquid culture conditions was specific and also exist in ointment format.

As a preliminary means of testing the combination ointment's performance against a broader panel of *S. aureus* strains, plate assays were expanded to include a contemporary methicillin resistant clinical isolate, USA300 which is neomycin resistant (MIC=128 μg ml$^{-1}$; data not shown), and strain BAA-1708 containing the mupA gene that confers high level mupirocin resistance (MIC>256 μg ml$^{-1}$; data not shown). As shown in FIG. 2B, mupirocin elicited a clear zone of USA300-LAC growth inhibition (14.0 (±4) cm$^2$). Interestingly, 1% neomycin ointment produced a small (3.6 (±0.25) cm$^2$) halo-like zone of inhibition despite the strain's resistance to the agent, indicating that the concentration tested is able to overcome the organism's resistance phenotype to a certain extent. Moreover, the combination treatment showed a significant increased inhibition zone (24.0 (±3) cm$^2$) in comparison to either agent alone. As shown in FIG. 2C, testing of the high level mupirocin resistant strain BAA-1708, demonstrated that the strain was resistant to 2% mupirocin ointment in comparison to both UAMS-1 and USA300 measures generating a slight zone of growth inhibition (3.6 (±1) cm$^2$). Conversely, 1% neomycin ointment elicited a clear zone of inhibition (4.8 (±1.1) cm$^2$), which was significantly increased by combination treatment (7.5 (±0.2) cm$^2$).

Taken together, these results indicate that mupirocin and neomycin are compatible in the ointment format tested here. Further, the combination of 2% mupirocin+1% neomycin exhibited significantly increased antimicrobial activity in comparison to either agent alone and displayed activity against all strains irrespective of their resistance profile. From these perspectives, it was hypothesized that the combination would be similarly therapeutically beneficial in host-environments that mupirocin (alone) is typically used for the prevention and/or therapeutic intervention of staphylococcal infections. But, as noted above and elaborated below, it was recognized that the RNase P inhibitor, RNPA2000, failed to display efficacy in host environments despite the agent's impressive in vitro antimicrobial properties, including superiority to neomycin in synergizing with mupirocin. Thus, it was recognized to be likely that neomycin would similarly fail in tests of the host environment.

Example 5

The Effects of Mupirocin and Neomycin on *S. aureus* Nasal Decolonization

A murine model of *S. aureus* nasal colonization was used to compare the antimicrobial efficacy of mupirocin, neomycin, and the two agents when applied in combination. To do so, the nasal passage of Balb-c mice were inoculated with ~1×10$^7$ colony forming units of *S. aureus* then treated three times a day for a total of three days, at which point the bacterial burden was measured and the antibiotic susceptibility of ten isolates from each animal was measured by MIC testing.

Figures 3A, 3B, 3C:
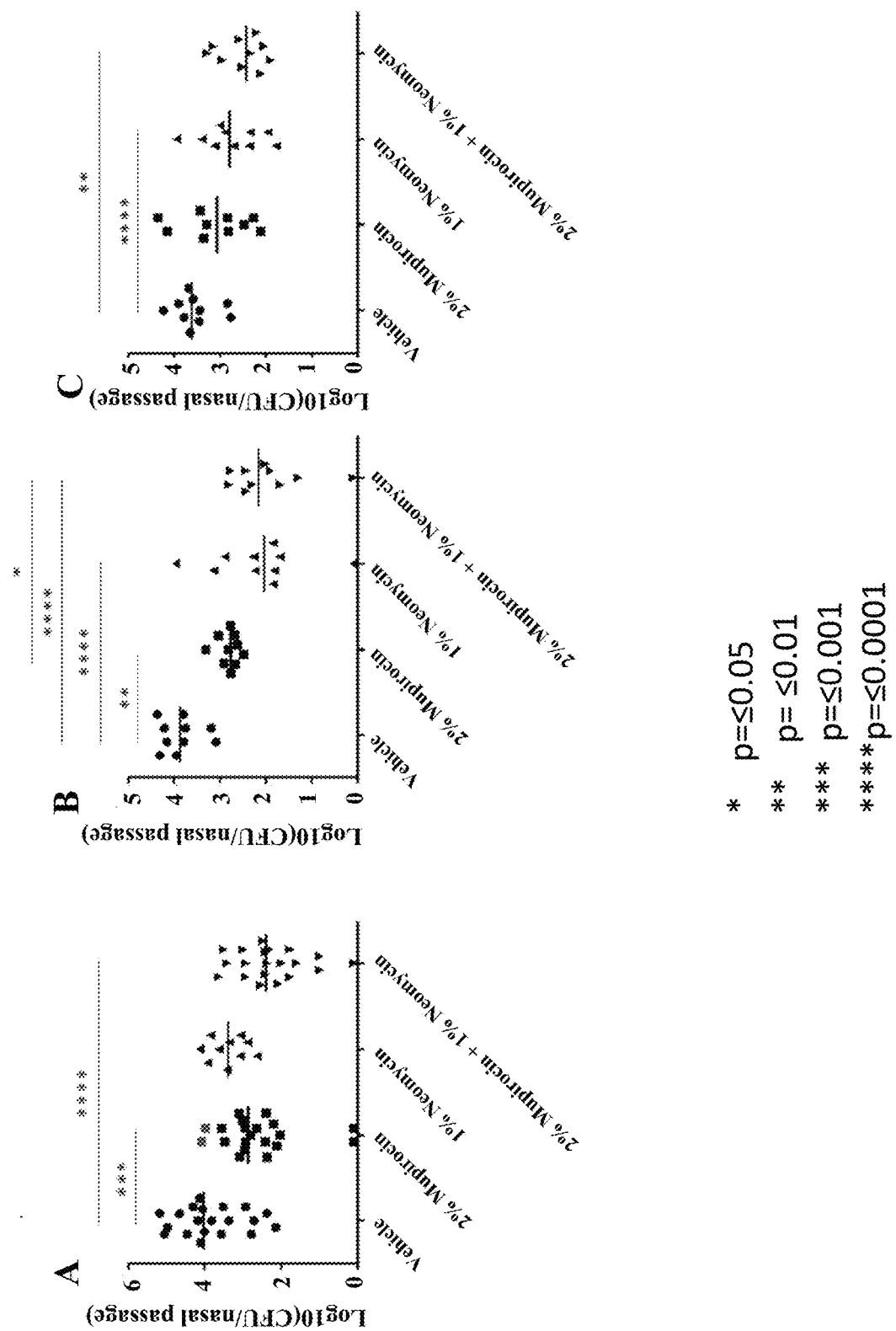
FIGS. 3A-3C show improved nasal decolonization effects by the combination treatment of mupirocin and neomycin.

Consistent with previous reports, 2% mupirocin treatment resulted in a 1-log reduction in *S. aureus* strain UAMS-1 colonization FIG. 3A. However, two mice displayed uncharacteristically higher-burdens in comparison to other cohort members (shown in red), which upon testing of these isolates were found to exhibit 4-fold increase in mupirocin tolerance (MIC of 0.5 µg ml$^{-1}$) in comparison to the inoculating strain as well as isolates from the other animals within the treatment group (MIC of 0.125 µg ml$^{-1}$), suggesting that mupirocin (alone) dosing selects for low-level resistant derivatives. While 1% neomycin treatment appeared to elicit decolonization, the effects were less than mupirocin (alone). Maximum significant decolonization was achieved with treatment with 2% mupirocin+1% neomycin and did not appear to select for low level antibiotic resistance. Similar results were observed for USA300 nasal decolonization (FIG. 3B). More specifically, 2% mupirocin treatment resulted in a 1-log decrease in bacterial burden, but did not appear to select for mupirocin tolerant derivatives. Treatment with 1% neomycin (alone) resulted in nearly a 2-log reduction in USA300 burden, but also elicited more variability than the mupirocin (alone) group, whereas the combination appeared to consistently reduce bacterial burden to the greatest extent (1.8-log reduction). A similar effect was also observed with tests of *S. aureus* strain BAA-1708, which despite displaying a high-level mupirocin resistant phenotype, exhibited a moderate reduction in burden (0.54 log) following mupirocin (alone) treatment, a 0.8 log reduction in 1% neomycin treated animals and a 1.2-log reduction following combination treatment (FIG. 3C).

Taken together these results indicate that combination topical application of 2% mupirocin+1% neomycin significantly improved *S. aureus* nasal decolonization for the three strains tested then either agent alone. Based on that observation, combined with the notoriously low resolution of the nasal models available, studies were expanded to evaluate the combination's performance in a murine wound model of *S. aureus* infection.

Example 6

The Effects of Mupirocin and Neomycin on *S. aureus* Wound Clearance

A murine dermal wound model was used to evaluate the decolonization properties of 2% mupirocin, 1% neomycin and 2% mupirocin+1% neomycin. To do so, a dermal wound was created on the back of Balb-c mice, inoculated with either *S. aureus* strain UAMS-1, USA300, or BAA-1708, and then treated with test agent suspended in PEG-based ointment twice a day for a total of 3 days, at which point bacterial burden was measured.

Figures 4A, 4B, 4C:
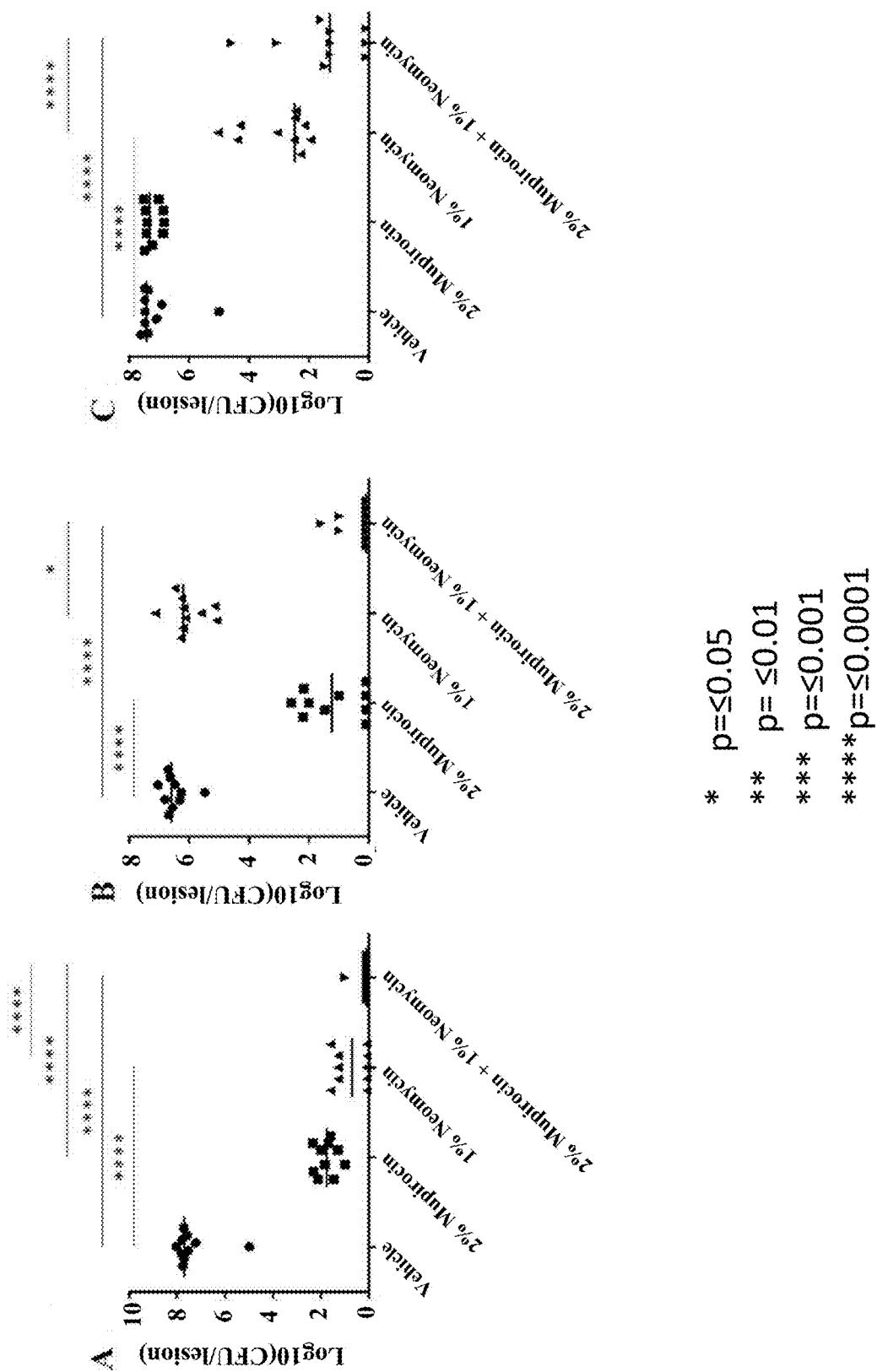
FIGS. 4A-4C show improved wound decolonization effects by the combination treatment of mupirocin and neomycin.

As shown in FIG. 4A, three day treatment with 2% mupirocin resulted in a nearly 6-log reduction in UAMS-1 colonization (1.8×10$^1$ cfu per lesion) of the wound site in comparison to animals that were treated with vehicle alone (7×10$^7$ cfu per lesion). One percent neomycin treatment exhibited improved clearance in comparison to mupirocin (alone), resulting in a 1×10$^1$ cfu per lesion with no bacteria recovered from 5 of the 10 (50%) of the animals within the treatment group. Combination treatment displayed the greatest efficacy. No bacteria recovered from 9 of the 10 animals (90%) treated with 2% mupirocin+1% neomycin, whereas a single UAMS-1 colony was recovered from the remaining animal (1×10$^1$ cfu). Testing of the neomycin resistant strain, USA300, showed that 2% mupirocin was effective, resulting in nearly a 5-log reduction in bacterial wound site burden, with no bacteria recovered from 4 of the 10 (40%) animals in the treatment group (FIG. 4B). While, neomycin treatment (alone) had minimal effects on decolonization, presumably due to the strain's neomycin resistance phenotype, the greatest efficacy was observed for the combination treated group, in which no USA300 cells were recovered from 7 of 10 (70%) of the animals tested. Similarly, the combination of mupirocin and neomycin displayed the greatest efficacy in tests of the mupirocin resistant strain BAA-1708 (FIG. 4C). More specifically, as expected, 2% mupirocin treatment (alone) did not reduce wound site colonization in comparison to vehicle treated cells, whereas neomycin treatment (alone) resulted in an approximately 5-log decrease in recoverable bacteria. The combination of mupirocin+neomycin produced the greatest reduction in colonization, resulting in a 7-log decrease in wound site bacteria and no recoverable bacteria in 3 of the 10 (30%) animals tested. Taken together, these results indicate that mupirocin+neomycin ointments are more effective in reducing wound site *S. aureus* burden than either agent alone and that the combination is capable of overcoming resistance to either agent.

Example 7

The Antimicrobial Potential of Mupirocin and Neomycin Combination Ointment Toward Other Bacterial Species Mupirocin and neomycin are predominately active toward Gram-positive and Gram-negative species, respectively. Consequently, it was predicted that the combination would display increased spectrum of activity in comparison to either agent alone, which would improve treatment options for polyclonal wound site infections composed of mixtures of both Gram-positive and negative organisms.

Figure 5:
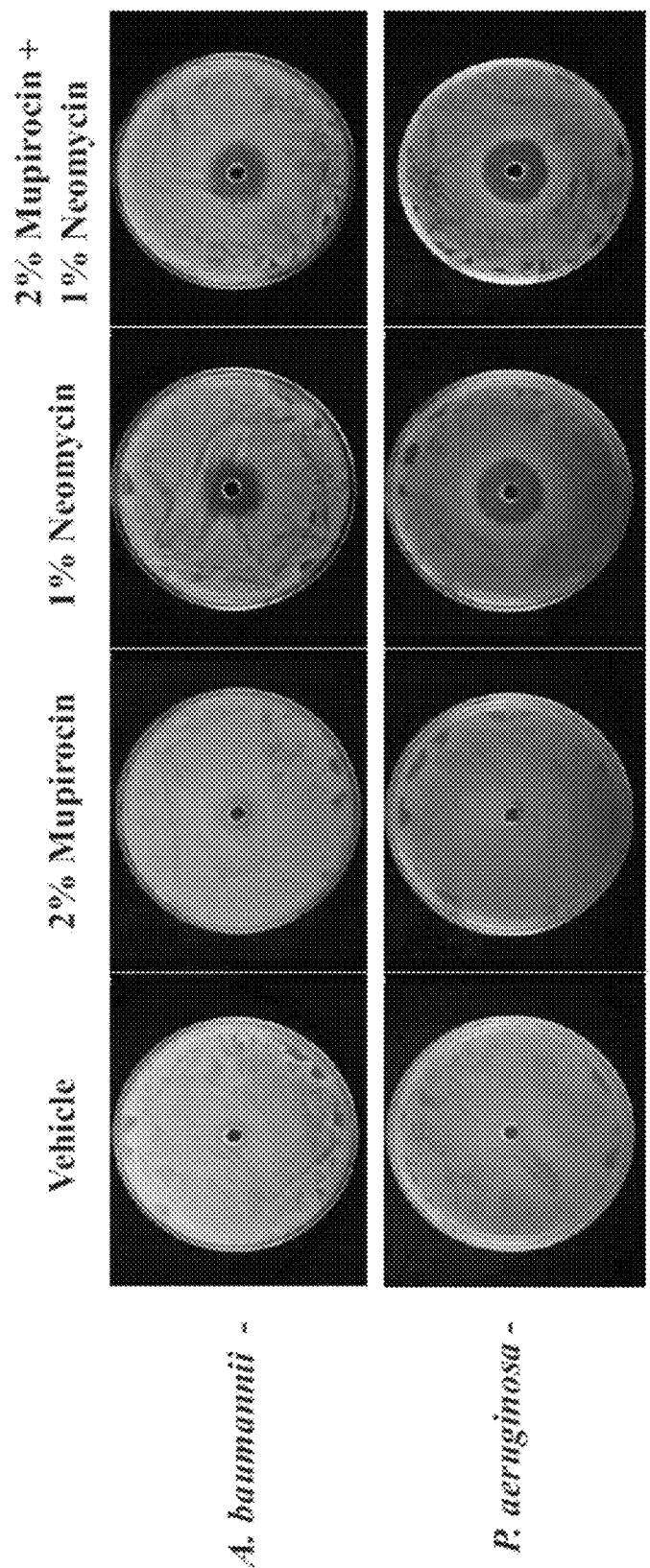
FIG. 5 shows antimicrobial activity towards other bacteria species by the combination treatment of mupirocin and neomycin.

As a preliminary test of that hypothesis, zone of inhibition assays were performed for 2% mupirocin, 1% neomycin and 2% mupirocin+1% neomycin using *A. baumannii* and *P. aeruginosa*, two Gram-negative organisms that are frequent causes of wound site infections. As shown in FIG. 5, 2% mupirocin ointment did not appear to restrict growth of *A. baumannii* strain 98-37-09 or *P. aeruginosa* strain PA01. Conversely, neomycin, both alone and in combination with mupirocin, restricted growth of both organisms, indicating that the combination of 2% mupirocin+1% neomycin may be useful in the prevention and/or treatment of complicated wound infections. Both agents, independently and in combination, also limited to similar extents growth of *S. epidermidis, Escherichia coli*, and *Streptococcus pyogenes* strains tested (data not shown).

Example 8

Effects of Mupirocin and Neomycin on Wound Healing

The above results indicate that combination ointments comprised of mupirocin and neomycin display improved antimicrobial efficacy, overcome mupirocin resistance, and are likely to exhibit increased spectrum of activity toward other bacterial species, in comparison to mupirocin (alone). It was considered that such a combination therapeutic would most likely be of value in the context of the wound setting. In that regard, although both mupirocin and neomycin are F.D.A. approved antibiotics for topical use, it was evaluated whether each agent, both alone and in combination, as a means to evaluate whether the mixture of both agents exhibited overt detrimental side effects at the wound site. To do so, dermal wounds were created and animals were treated with either vehicle, 2% mupirocin, 1% neomycin, or the combination (2% mupirocin+1% neomycin) twice daily for a total of 14 days. Each day, animals were assessed for alertness and grooming, weight and wound size.

Figures 6A, 6B, 6C:
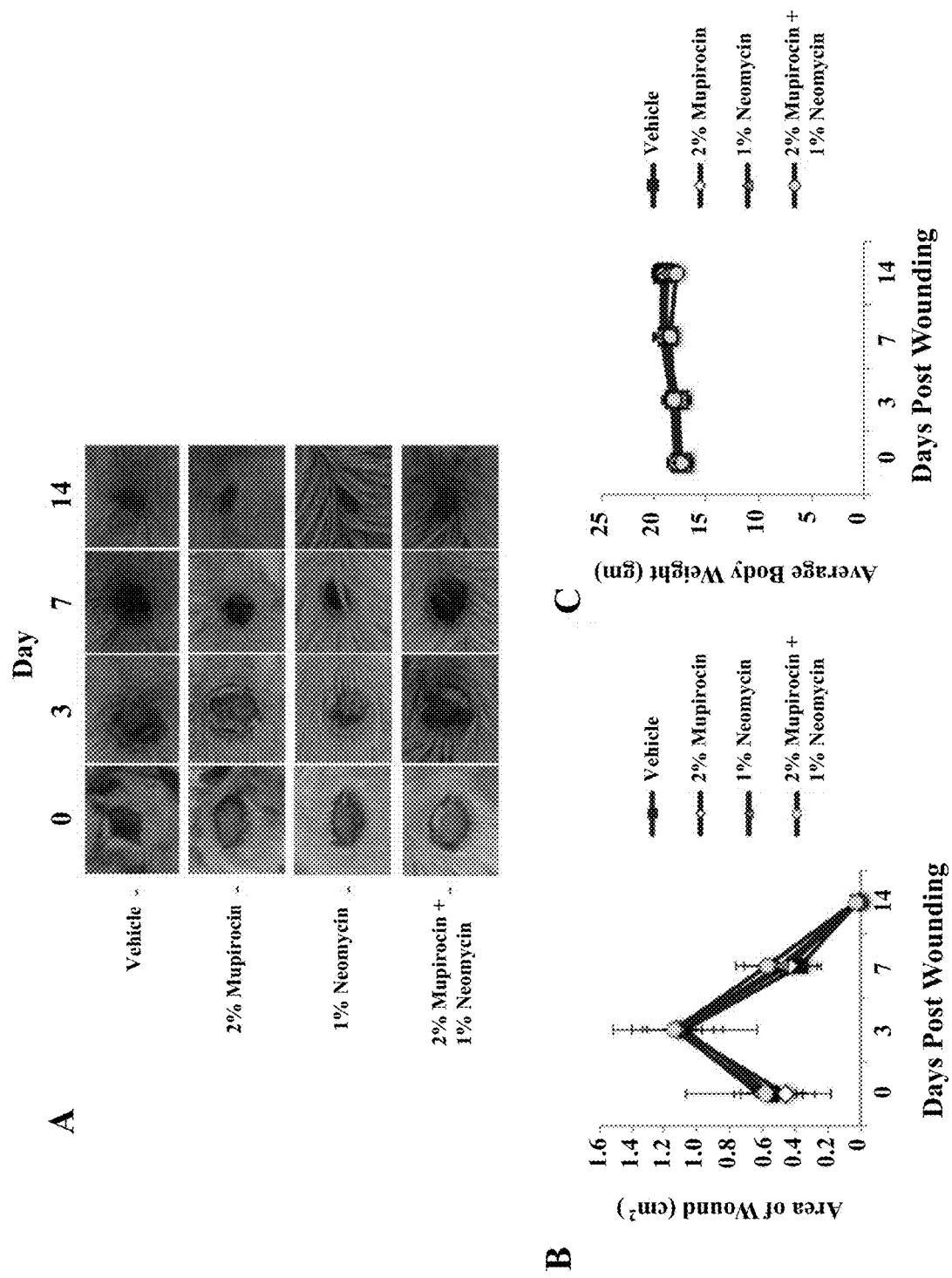
FIGS. 6A-6C show the combination of mupirocin and neomycin do not negatively affect wound healing, wound contraction or weight of treated animals.

No significant differences in wound contraction were observed for any of the treatment groups (N=3 for each treatment), in comparison to vehicle containing ointment (FIGS. 6A and 6B). Regardless of ointment used, wound size increased 3 days post-lesion formation and was followed by a linear increase in wound contraction, such that the wound healing was completed and hair growth had been restored at 14 days of treatment. Likewise, no significant differences in weight were recorded for any animals in any of the treatment groups (FIG. 6C).

Taken together these results demonstrate that the combination of mupirocin and neomycin is superior to that of either agent alone in terms of antimicrobial efficacy, overcoming antibiotic resistance, and antimicrobial spectrum of activity toward other bacterial species. The combination does not display any obvious animal cytotoxicity.

Example 9

The RNase P Inhibitor, RNPA2000, is not Efficacious in Murine Models of Nasal or Wound Decolonization.

Figures 7A, 7B:
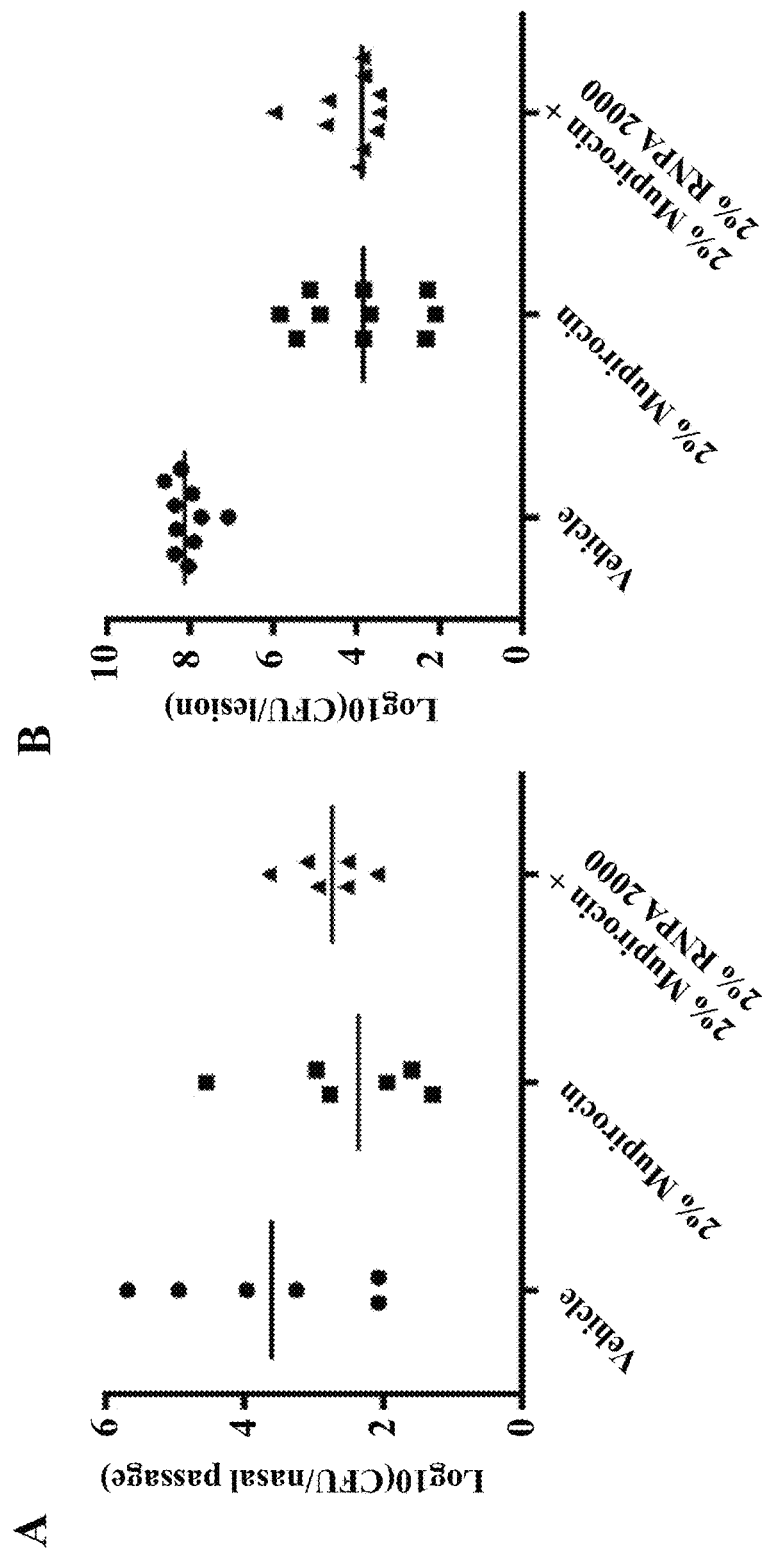
FIGS. 7A and 7B show comparative data on the antimicrobial effects of mupirocin and RNPA2000 combination treatment in nasal and wound decolonization.

As noted above, RNPA2000, has previously been identified as an RNase P inhibitor with tremendous therapeutic promise. Indeed, previous studies have shown that the agent displays antimicrobial activity against contemporary *S. aureus* clinical isolates as well as other problematic bacterial pathogens. Moreover, RNPA2000 exhibits superior synergy with mupirocin (FIC measures <0.5) in comparison to neomycin. Yet, RNPA2000 alone does not exhibit antimicrobial activity toward *S. aureus* strain UAMS-1 in murine models of nasal or wound decolonization (not shown). Likewise, RNPA2000 at any concentration tested in combination with mupirocin does not impose a synergistic effect in either of these models. Representative data is shown in FIGS. 7A and 7B, in which 2% mupirocin displays decolonization properties in the nasal and wound model, respectively, but even the highest concentration of the mixture that remains soluble in ointment formulation (2% mupirocin and 2% RNPA2000) fails to exhibit any synergistic effect.

From these perspectives, it was anticipated that RNPA2000's failure may be explained an absence of *S. aureus*' reliance on RNase P function in the in vivo setting, such that inhibiting the enzyme's activity through chemical intervention would have no deleterious effects on the organism when in the host environment and, consequently no therapeutic value. Extending the teachings of RNPA2000 it was similarly initially anticipated that the same could be true of combinations of mupirocin and neomycin. None the less, the grave void in the antibacterial pipeline and limited therapeutics under current development, superseded these predictions and prompted the course of neomycin+mupirocin combination characterization detailed above.

Example 10

Figure 8A:
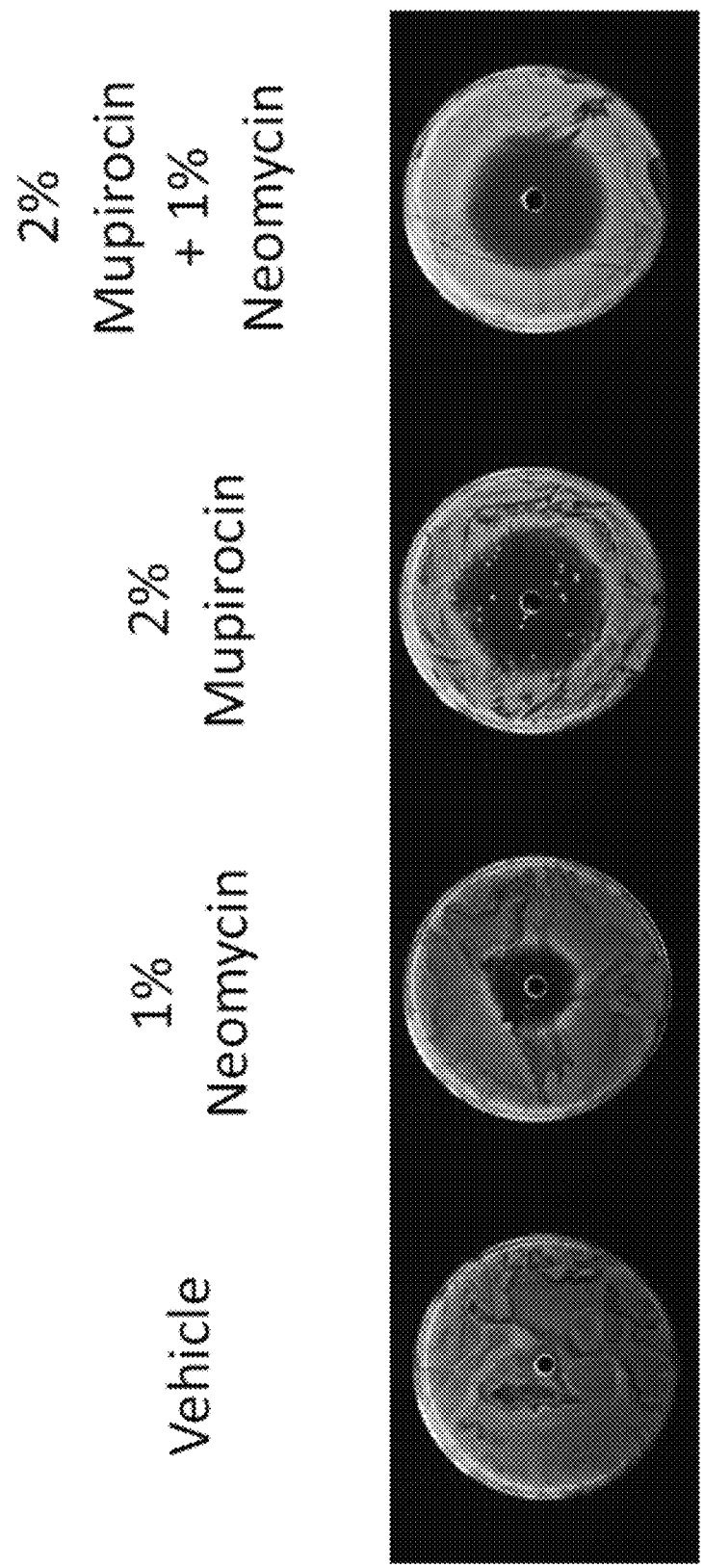
FIGS. 8A and 8B show antimicrobial activity towards *S aureus* from the clinical isolate by the combination treatment of mupirocin and neomycin.

The Antimicrobial Properties of Mupirocin and Neomycin Combination Ointment Against *S. aureus* in Human Clinical Isolate with Skin Infection Plate assays were conducted in clinical isolate where the human subjects had skin infection of *S. aureus*. Bacteria from the clinical isolate were spread on an agar plate and 40 microliters of ointment was loaded to the center. Zone of antibiotic-mediated cell growth inhibition is seen following 48 hr incubation. Ointments containing 1% Neomycin or 2% Mupirocin display resistant colony formation whereas the combination does not (FIG. 8A).

Figure 8B:
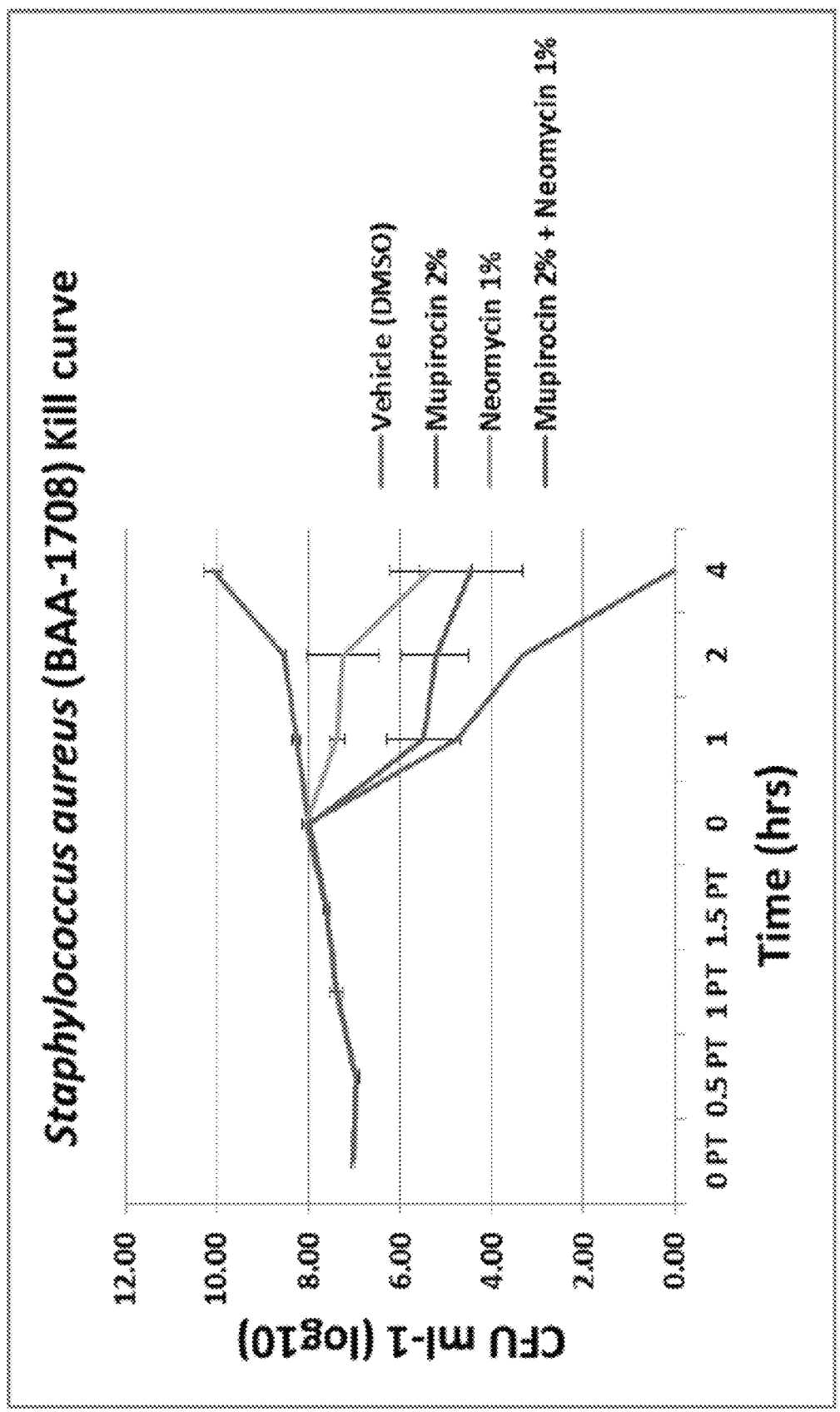

Bacteria in the clinical isolate were also tested for cell viability before and after the treatment with mupirocin, neomycin and the combination of the two (kill curve assay). *S. aureus* strain BAA-1708 was used for the tests. FIG. 8B shows cell viability counts of *S. aureus* strain BAA-1708 prior to treatment (PT) and hourly following treatment with either vehicle (DMSO; blue), 2% mupirocin (red), 1% neomycin (green) or the combination (purple). Results indicate that the combination exhibits a more rapid bactericidal effect than either agent alone. Standard deviation is shown.

What is claimed is:

1. A pharmaceutical composition comprising one or more pharmaceutically acceptable carriers and an anti-microbial therapeutic agent consisting of mupirocin and neomycin, wherein the weight ratio between mupirocin and neomycin is from about 1:10 to about 10:1.

2. The composition of claim 1, wherein the composition is for topical administration to a subject.

3. The composition of claim 2, wherein the subject has microbial infection.

4. The composition of claim 3, wherein the microbial infection is bacterial infection.

5. The composition of claim 1, wherein the weight ratio between mupirocin and neomycin is from about 1:4 to about 4:1.

6. The composition of claim 1, wherein the weight ratio between mupirocin and neomycin is about 4:1.

7. The composition of claim 1, wherein the weight ratio between mupirocin and neomycin is about 2:1.

8. The composition of claim 1, wherein the total concentration of mupirocin and neomycin in the composition is from about 1 wt. % to about 50 wt. %.

9. A topical formulation comprising one or more pharmaceutically acceptable carriers or excipients and an anti-microbial therapeutic agent consisting of mupirocin and neomycin, wherein the weight ratio between mupirocin and neomycin is from about 1:10 to about 10:1.

10. The topical formulation of claim 9, wherein the amount of mupirocin is from about 0.001 weight percent (wt. %) to about 8 wt. % per unit of the formulation.

11. The topical formulation of claim 9, wherein the amount of neomycin is from about 0.001 wt. % to about 8 wt. % per unit of the formulation.

12. The topical formulation of claim 11, wherein the weight ratio between mupirocin and neomycin is about 10:1 to about 1:10.

13. The topical formulation of claim 9, wherein the amount of mupirocin is from about 0.001 weight percent (wt. %) to about 4 wt. % per unit of the formulation and the amount of neomycin is from about 0.001 wt. % to about 4 wt. % per unit of the formulation.

14. The topical formulation of claim 13, wherein the weight ratio between mupirocin and neomycin is about 4:1 to about 1:4.

15. The topical formulation of claim 13, wherein the amount of mupirocin is from about 0.015 wt. % to about 2 wt. % per unit of the formulation and the amount of neomycin is from about 0.015 wt. % to about 2 wt. % per unit of the formulation.

16. The topical formulation of claim 13, wherein the amount of mupirocin is one selected from about 0.25 wt. %, about 1 wt. %, or about 2 wt. % per unit of the formulation and the amount of neomycin is one selected from about 0.25 wt. %, about 0.5 wt. %, or about 1 wt. % per unit of the formulation.

17. The topical formulation of claim 9, wherein the formulation is in the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray or a pad.

18. A method of decolonizing a microbial organism comprising contacting the microbial organism with a composition of claim 1.

19. A method of destroying or disrupting or inhibiting or reducing biofilm formation of a microbial organism comprising contacting the microbial organism with a composition of claim 1.

20. The method of claim 18, wherein the microbial organism is a bacterium.

21. A method of treating a microbial infection in a subject in need thereof comprising administering to the subject a therapeutically effective amount of the composition of claim 1.

22. The method of claim 21, wherein the microbial infection is a bacterial infection.

23. The method of claim 22, wherein the bacterial infection is characterized by colonization of a bacterium.

24. The method of claim 22, wherein the bacterial infection is characterized by biofilm formation.

25. The method of claim 21, wherein the microbial infection is a topical infection.

26. The method of claim 25, wherein the topical infection is selected from the group consisting of wound, ulcer and lesion.

27. The method of claim 19, wherein the microbial organism is a bacterium.

* * * * *